United States Patent

Yagihara et al.

[11] 4,187,110
[45] Feb. 5, 1980

[54] SILVER HALIDE PHOTOGRAPHIC LIGHT-SENSITIVE MATERIAL

[75] Inventors: Morio Yagihara; Mitsugu Tanaka; Takeshi Hirose; Toshiaki Aono, all of Minami-ashigara, Japan

[73] Assignee: Fuji Photo Film Co., Ltd., Minami-ashigara, Japan

[21] Appl. No.: 858,225

[22] Filed: Dec. 7, 1977

[30] Foreign Application Priority Data

Dec. 7, 1976 [JP] Japan .............................. 51-147027

[51] Int. Cl.² ............................................. G03C 1/06
[52] U.S. Cl. .................................. 430/544; 430/362; 430/957
[58] Field of Search .......................... 96/95, 100, 74

[56] References Cited

U.S. PATENT DOCUMENTS

| | | | |
|---|---|---|---|
| 3,632,345 | 1/1972 | Marx et al. | 96/95 |
| 4,015,989 | 4/1977 | Oishi et al. | 96/3 |
| 4,029,503 | 6/1977 | Fujiwhara et al. | 96/95 |
| 4,049,455 | 9/1977 | Kikuchi et al. | 96/95 |

*Primary Examiner*—J. Travis Brown
*Attorney, Agent, or Firm*—Sughrue, Rothwell, Mion, Zinn and Macpeak

[57] ABSTRACT

A silver halide photographic light-sensitive material containing a development inhibitor releasing compound, which is capable of forming a substantially colorless product, and which is represented by the following general formula (I):

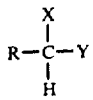

(I)

wherein X represents

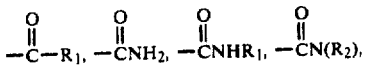

$-SO_2R_1$, $-SO_2OR_1$, $-SO_2NH_2$, $-SO_2NHR_1$, $-SO_2N(R_1)_2$, $-CN$, $-N^+(R_1)_3$ or

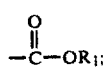

$R_1$ represents an aliphatic group, an aromatic group or a heterocyclic group and further two $R_1$ groups can combine and represent an atomic group necessary to form, together with the nitrogen atom to which they are attached, a nitrogen-containing heterocyclic group; R represents an aromatic group substituted with at least one of a nitro group, an acyl group, an alkoxycarbonyl group, a cyano group, a sulfamoyl group, a carbamoyl group, an aryloxycarbonyl group, an alkylsulfonyl group, an arylsulfonyl group, an alkoxysulfonyl group and an aryloxysulfonyl group; and Y represents a group capable of being released from the compound represented by the general formula (I) upon reaction with the oxidation product of a developing agent to provide an arylmercapto compound, a heterocyclic mercapto compound, a triazole compound, a benzotriazole compound or a naphthotriazole compound which has a development inhibiting effect.

7 Claims, 2 Drawing Figures

FIG I
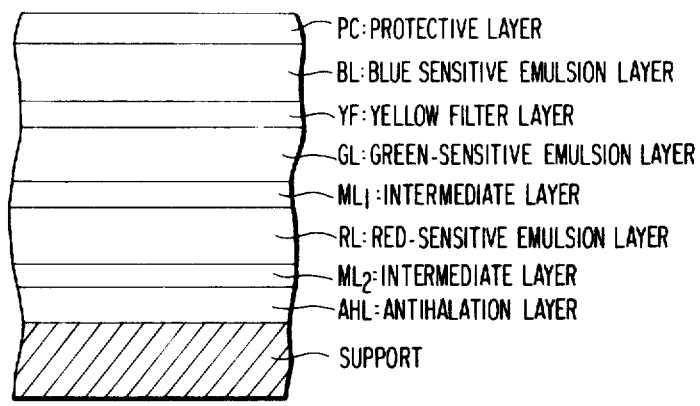
FIG 2
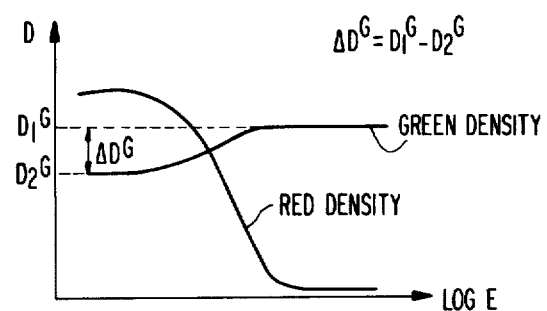

SILVER HALIDE PHOTOGRAPHIC LIGHT-SENSITIVE MATERIAL

BACKGROUND OF THE INVENTION

1. Field of the Invention

The present invention relates to a silver halide photographic light-sensitive material containing a compound capable of releasing a development inhibitor.

2. Description of the Prior Art

Incorporation of a compound which provides a development inhibitor in an amount depending on the optical density of an image formed upon development into a photographic light-sensitive material is known. Such a compound generally releases a development inhibitor by reaction with the oxidation product of a color developing agent. Typical development inhibitor releasing (DIR) compounds of this type include the so-called DIR couplers, the active site of which contains a group which exhibits a development inhibiting action when it is split from the active site. DIR couplers form dyes by coupling with the oxidation product of a color developing agent and release development inhibitors. Compounds such as those disclosed in U.S. Pat. Nos. 3,227,554, 3,701,783, 3,615,506, 3,617,291 and the like are known DIR couplers.

DIR couplers are employed for the purpose of controlling the image tone, reducing the graininess of the image, improving the sharpness of the image due to edge effects, improving the color reproduction due to interlayer effects, and the like, as is well known from the disclosure in the above-mentioned patent specifications.

However, in many cases, DIR couplers as described in U.S. Pat. No. 3,227,554, etc., do not exert the desired inhibiting effect resulting in a degradation of the photographic properties and storage properties because the dye yield upon development adversely affects the color reproduction unless the appropriate type of coupler residue and the appropriate amount of coupler are precisely chosen, and a convenient selection of a coupler residue for color reproduction restricts the permissible reactivity of the oxidation product of the color developing agent and the coupler. In addition, DIR couplers of this type have various disadvantages such as poor stability against ageing, they often exhibit a desensitization effect, they produce mottle resulting from contamination of the developer solution and the like.

The so-called non-color forming type of coupling compounds were developed with the intention of eliminating these disadvantages, which coupling compounds form essentially colorless products or colored products, whose color, however, changes and becomes essentially colorless in the course of photographic treatment upon undergoing a coupling reaction with the oxidation product of a color developing agent, and also yield a development inhibitor at the same time. Known compounds of this type are disclosed in German Patent Publication No. 1,547,640, German Patent Application (OLS) No. 2,362,752, and the like. While these compounds have advantageous properties, they also have some drawbacks. For example, the stain resulting from the products formed by the reaction of those compounds and the oxidation products of color developing agents is one drawback of the compounds. Their most serious drawback, however, is the low reactivity of the coupling compounds with the oxidation products of color developing agents. Accordingly, a large amount of these compounds must be employed because of their low reactivity and this results in a decrease in the photographic properties, a reduction in shelf life and a difficulty in the silver removal in a bleaching step.

In order to improve these drawbacks, the compounds as described in Japanese Patent Application (OPI) No. 122335/1974 (compounds in which a triazole ring or a diazole ring is bonded to the coupling position thereof through the nitrogen atom at the 1-position of the ring) and Japanese Patent Application No. 81141/1976 have been developed. While the photographic properties are improved to a certain extent using these compounds, it is desirable from a practical standpoint to provide a compound whose properties have been additionally improved particularly with respect to providing compounds having an extremely high coupling reactivity, compounds improving the graininess of the images in low optical density areas and compounds providing sufficiently improved interlayer color correction effects.

SUMMARY OF THE INVENTION

Therefore, a first object of the present invention is to provide a novel non-color forming coupling compound which rapidly reacts with the oxidation product of a developing agent to result in the release of a compound with a development inhibiting action.

A second object of the present invention is to provide a novel non-color forming coupling compound which provides not only intralayer effects but also provides sufficient interlayer effects, and, therefore, which provides a satisfactory color correction effect, particularly in low image density areas.

A third object of the present invention is to provide a novel non-color forming coupling compound which is stable against ageing, which does not exhibit a desensitization action, and which provides reduced mottle arising due to contamination of a developer solution.

A fourth object of the present invention is to provide a novel non-color forming coupling compound which is substantially colorless and which yields, upon reaction with the oxidation product of a developing agent, a substantially colorless product or a colored product which does not substantially contribute to the finished color image or which becomes substantially colorless during the course of photographic treatment.

A fifth object of the present invention is to provide a silver halide photographic light-sensitive material containing a novel non-color forming coupling compound.

A sixth object of the present invention is to provide a photographic processing solution containing a novel non-color forming coupling compound.

A seventh object of the present invention is to provide a method for forming an image wherein the photographic processing is carried out in the presence of a novel non-color forming coupling compound.

These objects of the present invention are attained with a compound which, upon reaction with the oxidation product of a color developing agent, simultaneously releases a compound having a development inhibiting action and forms substantially a colorless compound or a colored compound whose color is changed and such becomes substantially colorless in a developer solution or in another solution used in the photographic treatment subsequent to the development processing, and which is represented by the following general formula (I):

(I)

wherein X represents

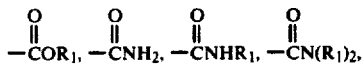

$-SO_2R_1$, $-SO_2OR_1$, $-SO_2N(R_1)_2$, $-SO_2NHR_1$, $-SO_2NH_2$, $-CN$, $-N^+(R_1)_3$ or

$R_1$ represents an aliphatic group, an aromatic group or a heterocyclic group, and further two $R_1$ groups can combine and represent an atomic group necessary to form, together with the nitrogen atom to which they are attached, a nitrogen-containing heterocyclic group; R represents an aromatic group substituted with at least one of a nitro group, an acyl group, an alkoxycarbonyl group, a cyano group, a sulfamoyl group, a carbamoyl group, an aryloxycarbonyl group, an alkylsulfonyl group, an arylsulfonyl group, an alkoxysulfonyl group and an aryloxysulfonyl group; and Y represents a group capable of being released from the compound represented by the general formula (I) upon reaction with the oxidation product of a color developing agent to provide an arylmercapto compound, a heterocyclic mercapto compound, a triazole compound, a benzotriazole compound or a naphthotriazole compound which has a development inhibiting effect.

BRIEF DESCRIPTION OF THE ACCOMPANYING DRAWINGS

FIG. 1 shows a cross sectional view of the layer structure of Samples 401 to 404 prepared as described hereinafter in Example 4.

FIG. 2 indicates the definition of $\Delta D^G$ which means the amount of interlayer effects obtained by exposure in the manner as described hereinafter in Example 4.

DETAILED DESCRIPTION OF THE INVENTION

The aliphatic group represented by $R_1$ is preferably an aliphatic group such as an alkyl group, an alkenyl group, etc., having 1 to 25 total carbon atoms which can be saturated or unsaturated, straight chain, branched chain or cyclic and can be substituted with one or more substituents, for example, a straight chain, branched chain or cyclic alkoxy group having 1 to 20 carbon atoms (such as a methoxy group, an isopropoxy group, etc.), a halogen atom (such as a chlorine atom, a bromine atom, etc.), a hydroxy group, a carboxy group, a sulfo group, a heterocyclic group (such as a tetrahydrofuran group, a pyridine group, etc.), a phenyl group, a benzyl group, a phenethyl group, and the like.

The aromatic group represented by $R_1$ is preferably a monocyclic or bicyclic aryl group having 6 to 35 total carbon atoms and suitable examples include an unsubstituted phenyl group or a phenyl group substituted with one or more substituents. Suitable substituents include monovalent substituents, for example, a halogen atom (such as a fluorine atom, a chlorine atom, a bromine atom, etc.), a nitro group, a cyano group, a thiocyano group, a hydroxy group, a straight chain, branched chain or cyclic alkoxy group (preferably an alkoxy group having 1 to 20 carbon atoms, such as a methoxy group, an isopropoxy group, an octoxy group, etc.), a monocyclic or bicyclic aryloxy group having 6 to 20 carbon atoms (such as a phenoxy group, a nitrophenoxy group, etc.), a straight chain, branched chain or cyclic alkyl group (preferably an alkyl group having 1 to 20 carbon atoms, such as a methyl group, an ethyl group, a dodecyl group, etc.), a straight chain, branched chain or cyclic alkenyl group (preferably an alkenyl group having 2 to 20 carbon atoms, such as an allyl group, etc.), a monocyclic or bicyclic aryl group (preferably an aryl group having 6 to 10 carbon atoms, such as a phenyl group, a tolyl group, etc.), an amino group (for example, an unsubstituted amino group, a straight chain, branched chain or cyclic alkylamino group having 1 to 20 carbon atoms, such as a diethylamino group, an octylamino group, etc.), a carboxy group, a straight chain, branched chain or cyclic acyl group (preferably an acyl group having 2 to 20 carbon atoms, such as an acetyl group, a decanoyl group, etc.), a straight chain, branched chain or cyclic alkoxycarbonyl group (preferably an alkoxycarbonyl group having 2 to 20 carbon atoms, in the alkyl moiety, such as a methoxycarbonyl group, a butoxycarbonyl group, an oxtoxycarbonyl group, a dodecyloxycarbonyl group, 2-phenylethoxycarbonyl group, a 2-methoxyethoxycarbonyl group, etc.), a monocyclic or bicyclic aryloxycarbonyl group (preferably an aryloxycarbonyl group having 6 to 20 carbon atoms in the aryl moiety, such as a phenoxycarbonyl group, a tolyloxycarbonyl group, etc.), a straight chain, branched chain or cyclic alkylcarbamoyl group (preferably an alkylcarbonyl group having 2 to 20 carbon atoms, such as an ethylcarbamoyl group, an octylcarbamoyl group, etc.), a monocyclic or bicyclic arylcarbamoyl group (preferably an arylcarbonyl group having 6 to 20 carbon atoms such as phenylcarbamoyl group, etc.), a straight chain, branched chain or cyclic acylamino group (preferably as acylamino group having 2 to 21 carbon atoms, such as an acetamido group, an octanamido group, 2,2,4-di-tert-pentylphenoxyacetamido group, etc.), a sulfo group, a straight chain, branched chain or cyclic alkylsulfonyl group (preferably an alkylsulfonyl group having 1 to 20 carbon atoms, such as a methylsulfonyl group, an octylsulfonyl group, etc.), a monocyclic or bicyclic arylsulfonyl group (preferably an arylsulfonyl group having 6 to 20 carbon atoms, such as a phenylsulfonyl group, a naphthylsulfonyl group, etc.), a straight chain, branched chain or cyclic alkoxysulfonyl group (preferably an alkoxysulfonyl group having 1 to 20 carbon atoms, such as a methoxysulfonyl group, an octoxysulfonyl group, etc.), a monocyclic or bicyclic aryloxysulfonyl group (preferably an aryloxysulfonyl group having 6 to 20 carbon atoms, such as a phenoxysulfonyl group, etc.), a sulfamoyl group (preferably a sulfamoyl group having 1 to 20 carbon atoms, such as a diethylsulfamoyl group, an octylsulfamoyl grouP, a methyloctadecylsulfamoyl group, etc.), a sulfonamido group (preferably an alkyl sulfonamido group having 1 to 20 carbon atoms, such as a methylsulfonamido group, an octylsulfonamido group, etc., an aryl sulfonamido group (preferably a phenylsulfonamide group, etc.)), and the like, or a divalent substituent which forms a condensed ring with the phenyl group (for example, a divalent group forming a naphthalene ring, etc.).

The heterocyclic group represented by $R_1$ includes a 5-membered or 6-membered heterocyclic group (for example, a 5-membered or 6-membered heterocyclic group containing at least one hetero atom such as a nitrogen atom, an oxygen atom, a sulfur atom, etc.) which group may have one or more benzene rings or naphthalene rings fused therewith. When two or more $R_1$ groups are present, each $R_1$ can be the same or different. Further, two $R_1$ groups in, for example, the $-N^+(R_1)_3$ group, the $-SO_2N(R_1)_2$ group or the like can combine and form together with the nitrogen atom to which they are attached, a saturated 5-membered or 6-membered heterocyclic ring, (for example, a piperidine ring, a pyrrolidine ring, a morpholine ring, etc.).

Particularly preferred examples of groups represented by X in the above-described general formula (I) are

groups wherein $R_1$ represents a phenyl group which can be substituted with one or more substituents, which may be the same or different, as described above for the aryl group represented by $R_1$.

The aromatic group having at least one substituent represented by R in the general formula (I) can be represented by the following general formula (II):

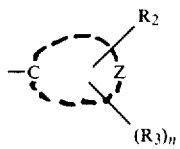

wherein Z represents an atomic group necessary to form, together with the carbon atom, a monocyclic or bicyclic aryl group having 6 to 20 carbon atoms; $R_2$ represents a nitro group, a cyano group, an acyl group (preferably an alkanoyl group having 2 to 16 carbon atoms, such as an acetyl group, a decanoyl group, etc. an aroyl group such as a benzoyl group, etc.), a straight chain, branched chain or cyclic alkoxycarbonyl group (preferably an alkoxycarbonyl group having 1 to 20 carbon atoms in the alkyl moiety, such as a methoxycarbonyl group, a butoxycarbonyl group, an octoxycarbonyl group, a dodecyloxycarbonyl group, a 2-phenylethyloxycarbonyl group, a 2-methoxyethoxycarbonyl group, etc.), a monocyclic or bicyclic aryloxycarbonyl group (preferably an aryloxycarbonyl group having 6 to 20 carbon atoms in the aryl moiety, such as a phenoxycarbonyl group, a tolyloxycarbonyl group, etc.), a carbamoyl group (preferably an alkylcarbamoyl group having 2 to 20 carbon atoms, such as a methylcarbamoyl group, an octylcarbamoyl group, etc. an arylcarbamoyl group such as a phenylcarbamoyl group, etc.), a sulfamoyl group (preferably an alkylsulfamoyl group having 1 to 20 carbon atoms, such as a diethylsulfamoyl group, an octylsulfamoyl group, a methyloctadecylsulfamoyl group, etc. an arylsulfamoyl group, such as a phenylsulfamoyl group, etc.), a straight chain, branched chain or cyclic alkylsulfonyl group (preferably an alkylsulfonyl group having 1 to 20 carbon atoms, such as a methylsulfonyl group, an octylsulfonyl group, etc.), a monocyclic or bicyclic arylsulfonyl group (preferably an arylsulfonyl group having 6 to 20 carbon atoms, such as a phenylsulfonyl group, a naphthylsulfonyl group, etc.), a straight chain, branched chain or cyclic alkoxysulfonyl group (preferably an alkoxysulfonyl group having 1 to 20 carbon atoms, such as a methoxysulfonyl group, an octoxysulfonyl group, etc.) or a monocyclic or bicyclic aryloxysulfonyl group (preferably an aryloxysulfonyl group having 6 to 20 carbon atoms, such as a phenoxysulfonyl group, etc.); $R_3$ represents a hydrogen atom, a halogen atom (such as a fluorine atom, a chlorine atom, a bromine atom, etc.), a nitro group, a cyano group, a thiocyano group, a hydroxy group, a straight chain, branched chain or cyclic alkoxy group (preferably an alkoxy group having 1 to 15 carbon atoms, such as a methoxy group, an isopropoxy group, an octoxy group, etc.), a monocyclic or bicyclic aryloxy group (such as a phenoxy group, a nitrophenoxy group, etc.), a straight chain, branched chain or cyclic alkyl group (preferably an alkyl group having 1 to 15 carbon atoms, such as a methyl group, an ethyl group, a dodecyl group, etc.), a straight chain, branched chain or cyclic alkenyl group (preferably an alkenyl group having 2 to 15 carbon atoms, such as an allyl group, etc.), a monocyclic or bicyclic aryl group (preferably an aryl group having 6 to 10 carbon atoms, such as a phenyl group, a tolyl group, etc.), an amino group (for example, an unsubstituted amino grouP, a straight chain, branched chain or cyclic alkylamino group having 1 to 15 carbon atoms, such as a diethylamino group, an octylamino group, etc.), a carboxy group, an acyl group (preferably a straight chain, branched chain or cyclic alkanoyl group having 2 to 16 carbon atoms, such as an acetyl group, a decanoyl group, etc. an aroyl group such as a benzoyl group, etc.) a straight chain, branched chain or cyclic alkoxycarbonyl group (preferably an alkoxycarbonyl group having 1 to 20 carbon atoms in the alkyl moiety, such as a methoxycarbonyl group, a butoxycarbonyl group, an octoxycarbonyl group, a dodecyloxycarbonyl group, a 2-phenylethyloxycarbonyl group, a 2-methoxyethoxycarbonyl group, etc.), a monocyclic or bicyclic aryloxycarbonyl group (preferably an aryloxycarbonyl group having 6 to 20 carbon atoms in the aryl moiety, such as a phenoxycarbonyl group, a tolyoxycarbonyl group, etc.), a carbamoyl group (for example, a straight chain, branched chain or cyclic alkylcarbamoyl group such as an ethylcarbamoyl group, an octylcarbamoyl group, etc. an arylcarbamoyl group such as a phenylcarbamoyl group, etc.), an acylamino group (preferably a straight chain, branched chain or cyclic alkanoylamino group having 2 to 21 carbon atoms, such as an acetamido group, an octanamido group, a 2,4-di-tert-pentylphenoxyacetamido group, etc. an aroylamino group such as a benzoylamino group, etc.), a sulfo group, a straight chain, branched chain or cyclic alkylsulfonyl group (preferably an alkylsulfonyl group having 1 to 15 carbon atoms, such as a methylsulfonyl group, an octylsulfonyl group, etc.), a monocyclic or bicyclic arylsulfonyl group (preferably an arylsulfonyl group having 6 to 20 carbon atoms, such as a phenylsulfonyl group, a naphthylsulfonyl group, etc.), a straight chain, branched chain or cyclic alkoxysulfonyl group (preferably an alkoxysulfonyl group having 1 to 15 carbon atoms, such as a methoxysulfonyl group, an octoxysulfonyl group, etc.), a monocyclic or bicyclic aryloxysulfonyl group (preferably an aryloxysulfonyl group having 6 to 20 carbon atoms, such as a phenoxysulfonyl group, etc.), a sulfamoyl group (preferably an alkyl sulfamoyl group having 1 to 15 carbon atoms, such as a diethylsulfamoyl group, an octylsulfamoyl group, a methyloctadecylsulfamoyl group, etc. an arylsulfamoyl group such as a phenylsulfamoyl group, etc.), a sulfonamido group (preferably an alkylsulfonamido group having 1 to 15 carbon atoms, such as a methylsulfonamido group, an octylsulfonamido group, etc. an arylsulfonamido group such as a phenylsulfonamido group, etc.), and the like; n represents an integer of 1 to 4.

By the introduction of the above-described $R_2$ group into the aryl groups as a substituent, the coupling activity of the compound extremely increases so that the objects of the present invention are achieved.

Y represents a group capble of being released from the compound represented by the general formula (I) upon reaction with the oxidation product of a developing agent to form an arylmercapto compound, a heterocyclic mercapto compound, a triazole compound, a benzotriazole compound or a naphthotriazole compound which has a development inhibiting effect.

Examples of heterocyclic mercapto compounds formed on release of Y include, for example, a mercaptotetrazole type compound (for example, 1-phenyl-5-mercaptotetrazole, 1-nitrophenyl-2-mercaptotetrazole, 1-naphthyl-5-mercaptotetrazole, etc.), a mercaptothiazole type compound (for example, 2-mercaptobenzothiazole, 2-mercaptonaphthothiazole, etc), a mercaptoxadiazole type compound (for example, 5-mercapto-1,2,4-oxadiazole, etc.), a mercaptopyrimidine type compound (for example, 4-mercaptopyrimidine, etc.), a mercaptothiadiazole type compound (for example, 2-mercapto-1,3,4-thiadiazole, etc.), a mercaptotriazine type compound (for example, 2-mercapto-1,3,5-triazine, etc.), a mercaptotriazole type compound (for example, 3-mercapto-1,2,4-triazole, etc.), a mercaptopiperidine type compound and a mercaptotetrazaindene type compound. Examples of the arylmercapto compounds formed on release of Y include, for example, a mercaptobenzene type compound (for example, 1-mercapto-2-benzoic acid, 1-mercapto-2-nitrobenzene, 1-mercapto-3-heptadecanoylaminobenzene, etc.). Of these compounds, 1-phenyl-5-mercaptotetrazole, 1-nitrophenyl-2-mercaptotetrazole are particularly advantageous.

The triazole compound, the benzotriazole compound and the naphthotriazole compound formed on release of Y can have one or more substituents. Suitable substituents include a halogen atom (such as a fluorine atom, a chlorine atom, a bromine atom, etc.), a straight chain, branched chain or cyclic acyl group (preferably an acyl group having 2 to 20 carbon atoms, such as an acetyl group, a decanoyl group, etc.), a straight chain, branched chain or cyclic alkoxycarbonyl group (preferably an alkoxycarbonyl group having 1 to 20 carbon atoms in the alkyl moiety, such as a methoxycarbonyl group, a butoxycarbonyl group, an octoxycarbonyl group, a dodecyloxycarbonyl group, a 2-phenylethoxycarbonyl group, a 2-methoxyethoxycarbonyl group, etc.), a hydroxy group, a carboxy group, a nitro group, a cyano group, a monocyclic or bicyclic aryl group (preferably an aryl group having 6 to 35 carbon atoms, such as a phenyl group, a naphthyl group, a tolyl group, etc.), a straight chain, branched chain or cyclic alkoxy group (preferably an alkoxy group having 1 to 20 carbon atoms, such as a methoxy group, an isopropoxy group, an octoxy group, etc.), a monocyclic or bicyclic aryloxy group (such as a phenoxy group, a chlorophenoxy group, a nitrophenoxy group, etc.), a acylamino group (preferably a straight chain, branched chain or cyclic alkanoylamino group having 2 to 21 carbon atoms, such as an acetamido group, an octanamido group, a 2,4-di-tert-pentylphenoxyacetamido group, etc. an aroylamino group such as a benozylamino group, etc.), a sulfo group, an amino group (for example, an unsubstituted amino group, a straight chain, branched chain or cyclic alkylamino group having 1 to 20 carbon atoms, such as a diethylamino group, an octylamino group, etc.), a straight chain, branched chain or cyclic alkyl group (preferably an alkyl group having 1 to 20 carbon atoms, such as a methyl group, an ethyl group, a dodecyl group, etc.), a straight chain, branched chain or cyclic alkenyl group (preferably an alkenyl group having 2 to 20 carbon atoms, such as an allyl group, etc.), a sulfamoyl group (preferably an alkyl sulfamoyl group having 1 to 20 carbon atoms, such as a diethylsulfamoyl group, an octylsulfamoyl group, a methyloctadecylsulfamoyl group, etc. an arylsulfamoyl group such as a phenylsulfamoyl group, etc.), a sulfonamido group (preferably an alkylsulfonamido group having 1 to 20 carbon atoms, such as a methanesulfonamido group, a toluenesulfonamido group, a hexadecanesulfonamido group, etc., an arylsulfonamido group such as a phenylsulfonamido group etc.), a carbamoyl group (preferably an alkylcarbamoyl group having 2 to 20 carbon atoms, such as an ethylcarbamoyl group, and octylcarbamoyl group, etc. an arylcarbamoyl group such as a phenylcarbamoyl group, etc.), a ureido group having 1 to 20 carbon atoms, (for example, a straight chain, branched chain or cyclic alkylureido group, monocyclic or bicyclic arylureido group, a heterocyclic ureido group, etc.), a straight chain, branched chain or cyclic alkoxycarbonylamino group, a straight chain, branched chain or cyclic alkylthio group (preferably an alkylthio group having 1 to 20 carbon atoms, such as a methylthio group, a butylthio group, a hexadecylthio group, etc.), a monocyclic or bicyclic arylthio group (such as a phenyl group), an alicyclic hydrocarbon group having 4 to 7 carbon atoms (such as a cyclohexyl group, a cyclopentyl group, etc.), a thiocyano group, an aryloxycarbonyl group (preferably a monocyclic or bicyclic aryloxycarbonyl group having 6 to 20 carbon atoms in the aryl moiety, such as a phenoxycarbonyl group, a tolyloxycarbonyl group, etc.), a straight chain, branched chain or cyclic alkylsulfonyl group (preferably an alkylsulfonyl group having 1 to 20 carbon atoms, such as a methylsulfonyl group, an octylsulfonyl group, etc.), a monocyclic or bicyclic arylsulfonyl group (preferably an arylsulfonyl group having 6 to 20 carbon atoms, such as a phenylsulfonyl group, a naphthylsulfonyl group, etc.), a straight chain, branched chain or cyclic alkoxysulfonyl group (preferably an alkoxysulfonyl group having 1 to 20 carbon atoms, such as a methoxysulfonyl group, an octoxysulfonyl group, etc.), a monocyclic or bicyclic aryloxysulfonyl group (preferably an aryloxysulfonyl group having 6 to 20 carbon atoms, such as a phenoxysulfonyl group, etc.), an imido group (such as a succinimido group, a phthalimido group, an octadecenylsuccinimido group, etc.), a 5- or 6-membered heterocyclic group containing one or more of nitrogen, oxygen and sulfur atoms as hetero atoms (such as a 1,3-thiazolin-2-thion-3-yl group, a pyridyl group, etc.), an aralkyl group (preferably an aralkyl group having 7 to 30 carbon atoms, such as a benzyl group, a phenylethyl group, etc.), an aralkoxy group (preferably an aralkoxy group having 7 to 30 carbon atoms, such as a benzyloxy group, a phenethyloxy group, etc.), an imino group, and a group represented by the general formula (III) or (IV):

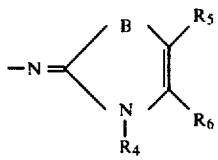
(III)

wherein B represents a sulfur atom, a selenium atom or an oxygen atom; $R_4$ represents an alkyl group having 1 to 20 carbon atoms (for example, a methyl group, a decyl group, a pentadecyl group, etc.); and $R_5$ and $R_6$ each represents a hydrogen atom, an alkyl group having 1 to 20 carbon atoms (for example, a methyl group, a decyl group, a pentadecyl group, etc.), an alkoxy group having 1 to 20 carbon atoms (such as a methoxy group, a decyloxy group, a pentadecyloxy group, etc.), a hydroxy group or a phenyl group and $R_5$ and $R_6$ can combine and represent an atomic group necessary to form a benzene ring or a naphthalene ring,

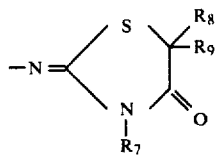
(IV)

wherein $R_7$ represents an alkyl group (having 1 to 20 carbon atoms such as a methyl group, a decyl group, a pentadecyl group, etc.) or an aromatic group (such as a phenyl group, etc.); and $R_8$ and $R_9$, which may be the same or different, each represents a hydrogen atom, an alkyl group (having 1 to 20 carbon atoms such as a methyl group, a decyl group, a pentadecyl group, etc.) or a phenyl group. When two or more substituents are present, the substituents can be the same or different.

Of the groups represented by Y, a benzotriazole group which is bonded at the 1- or 2-position thereof is particularly preferred and the benzotriazole group can have one or more substituents which may be the same or different. Suitable substituents include, for example, a halogen atom, an acyl group, an alkoxycarbonyl group, a carboxy group, a sulfo group, a nitro group, an acylamino group, a ureido group, a carbamoyl group, a sulfamoyl group, an alkoxy group, an aryloxy group, an alkyl group, a heterocyclic group, an aralkyloxy group, an aryl group, an amino group, an imino group, a group represented by the above-described general formula (III) or (IV), etc. Specific examples of suitable substituents are the same as those described above for the triazole compound, the benzotriazole compound and the naphthotriazole compound.

Of the substituents represented by the general formula (III), a group represented by the following general formula (IIIA):

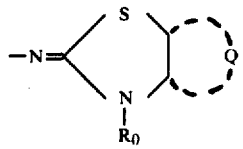

wherein $R_0$ represents an aliphatic group [for example, an alkyl group (such as a methyl group, an ethyl group, a propyl group, a butyl group, etc.), a substituted alkyl group (such as a sulfopropyl group, etc.), an alkenyl group (such as a allyl group, etc.), and the like], an aralkyl group (for example, a benzyl group, a phenethyl group, etc.) or an aryl group (for example, a phenyl group, etc.); and Q represents an atomic group necessary to form an aromatic ring (for example, a benzene ring, etc.) which can have one or more substituents, for example, an alkyl group (such as a methyl group, an ethyl group, a propyl group, etc.), an alkoxy group (such as a methoxy group, an ethoxy group, etc.), a halogen atom (such as a chlorine atom, a bromine atom, etc.), and the like, is preferred as the substituents of the benzotriazole group.

Representative examples of benzotriazole type releasable groups are, for example, a 5- or 6-benzyloxybenzotriazolyl group, a 5- or 6-octanamidobenzotriazolyl group, a 5- or 6-(3-methylbenzothiazolinyliden)aminobenzotriazolyl group, a 5- or 6-(3-ethylbenzothiazolinyliden)aminobenzotriazolyl group, a 5- or 6-(3-benzylbenzothiazolinyliden)aminobenzotriazolyl group, a quinoxalino [2,3-f]benzotriazolyl group, and the like.

The non-color forming coupling compound according to the present invention has remarkably superior properties in comparison with known non-color forming coupling compounds in that it has a high coupling activity and extremely high development inhibiting effect, in that it provides reduced graininess and improved sharpness, in that the compound per se is stable and thus light-sensitive materials containing the compound have improved ageing properties, and further in that, when the non-color forming coupling compound of the present invention is used in a light-sensitive material, the color of the product formed by the reaction of the non-color forming coupling compound with the oxidation product of a color developing agent hardly makes any contribution to color images. It can, therefore, be used without concern in a layer such as a green-sensitive layer or a red-sensitive layer containing a coupler which forms a dye having a color different from that of the dye formed from the compound of the present invention. That is, the coupling compound of the present invention can be used simultaneously in each of the three different spectrally sensitive layers in a color photographic film, which is extremely advantageous from the viewpoint of cost and emulsion design. Furthermore, using the non-color forming coupling compound of the present invention, improvements in graininess, particularly in the low density areas, and large interlayer color correction effects are achieved.

Moreover, the silver removal ability in the bleaching step is not deteriorated when the coupling compound of the present invention is used.

Typical examples of the non-color forming coupling compounds represented by the general formula (I) are illustrated below, but the present invention should not be construed as being limited to these compounds.

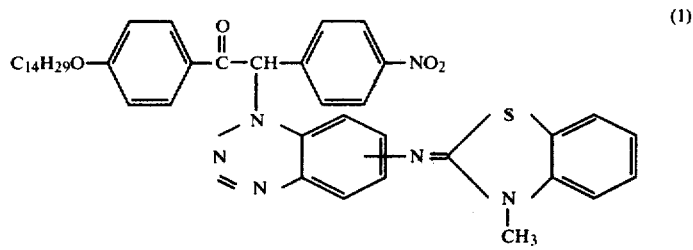
(1)
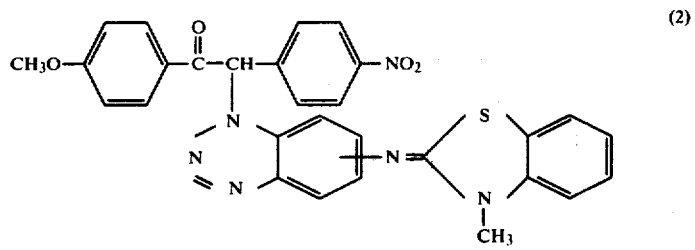
(2)
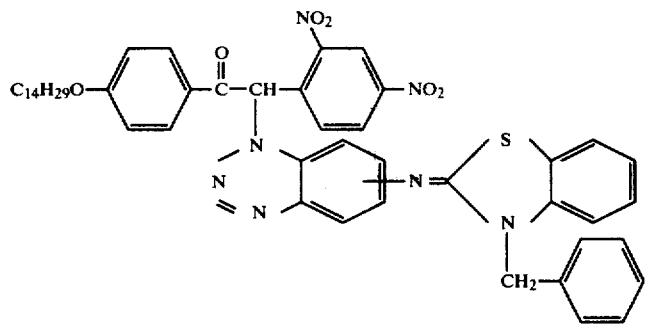
(3)
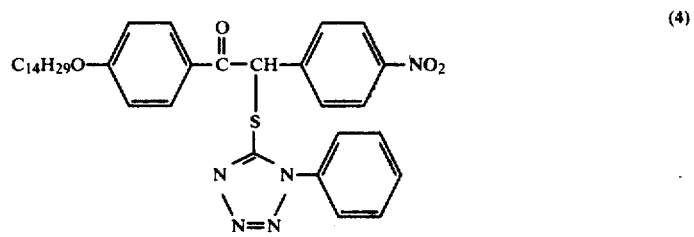
(4)
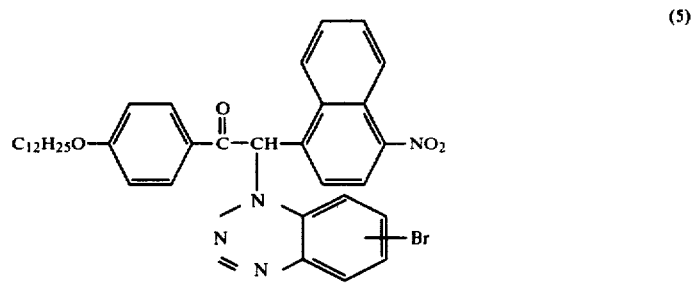
(5)
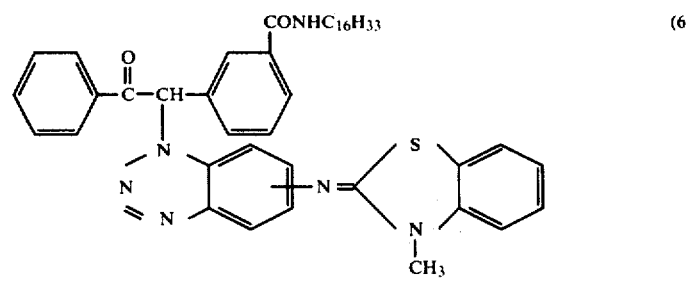
(6)

-continued
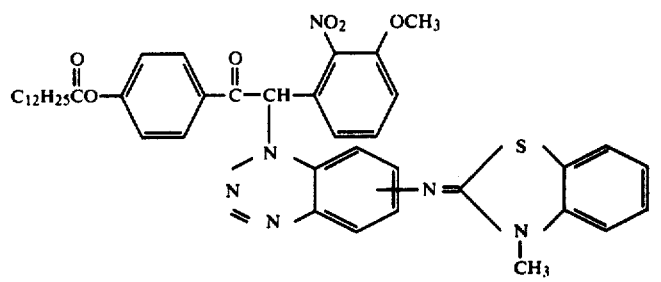
(7)
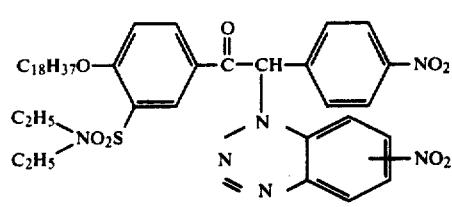
(8)
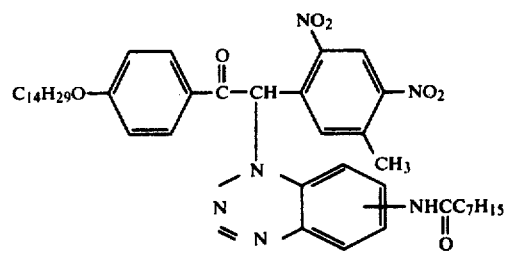
(9)
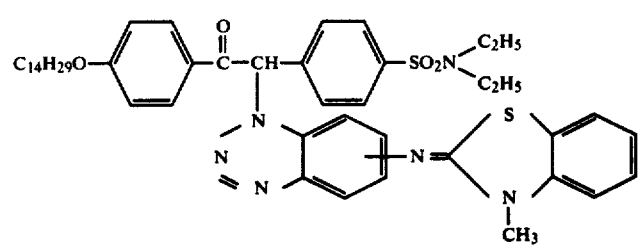
(10)
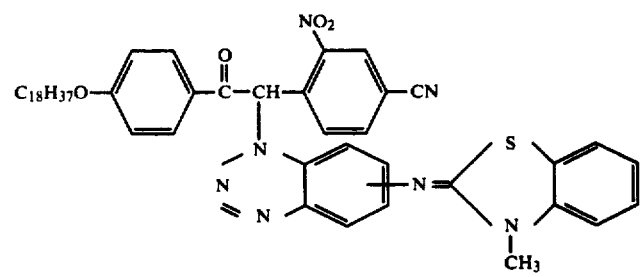
(11)
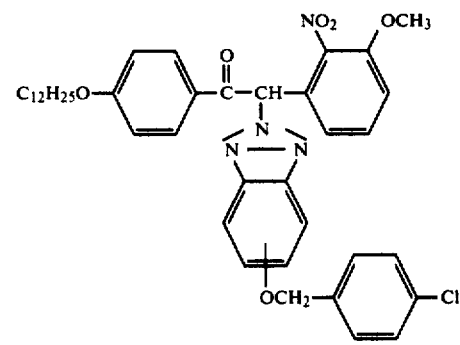
(12)

-continued
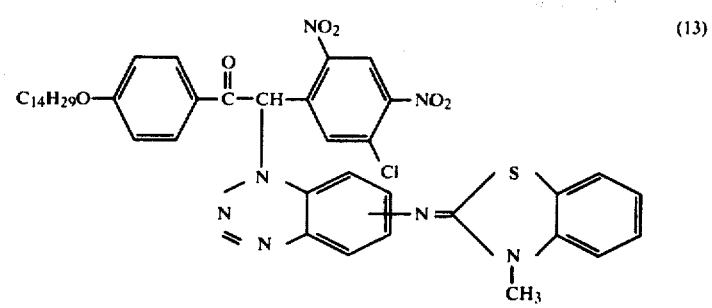 (13)
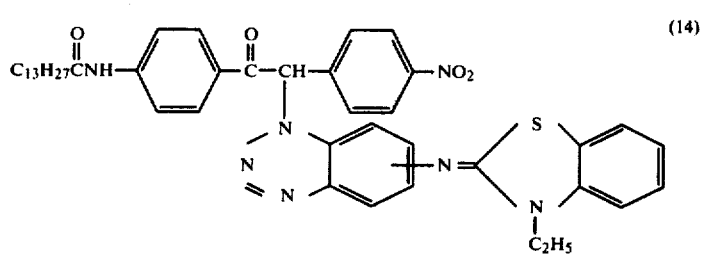 (14)
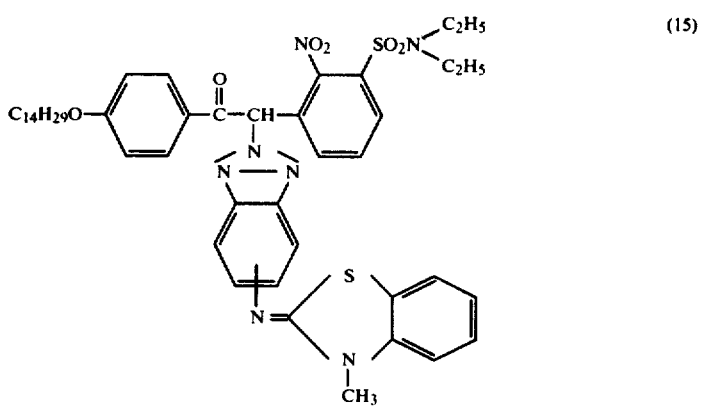 (15)
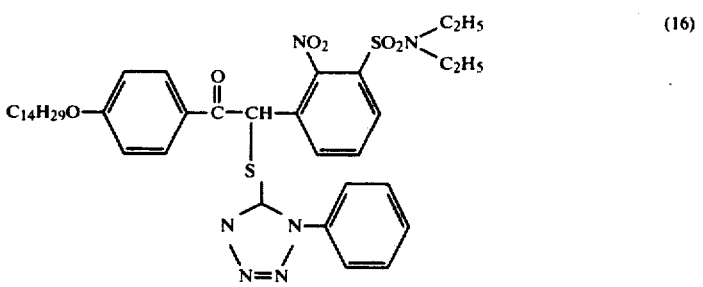 (16)
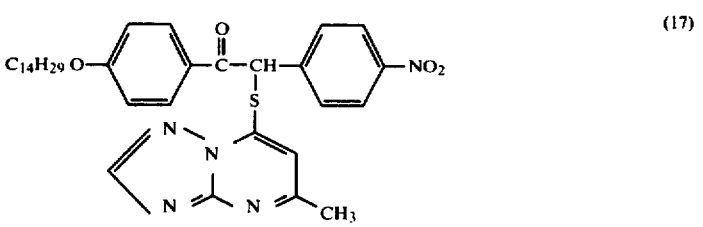 (17)
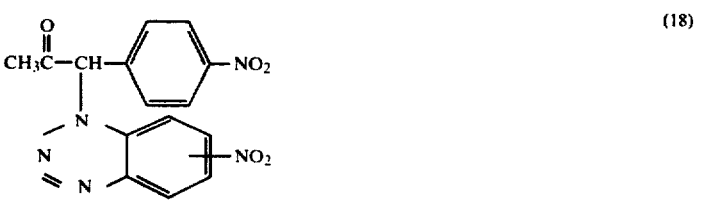 (18)

-continued
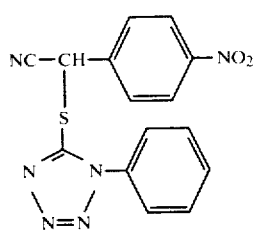
(19)
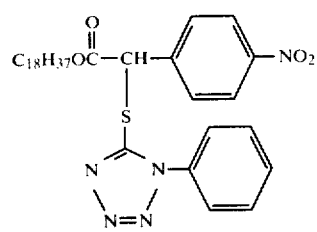
(20)
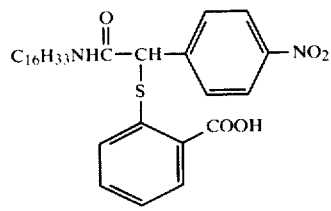
(21)
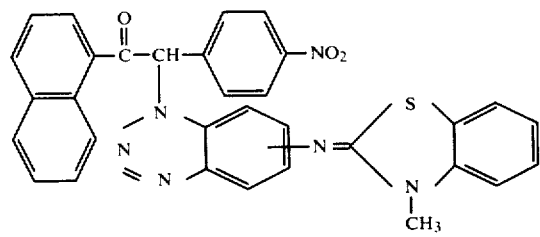
(22)
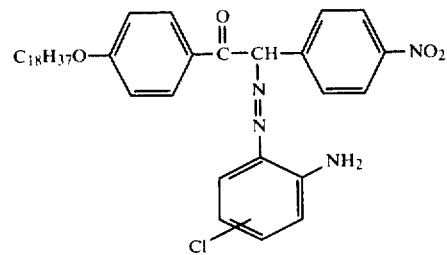
(23)
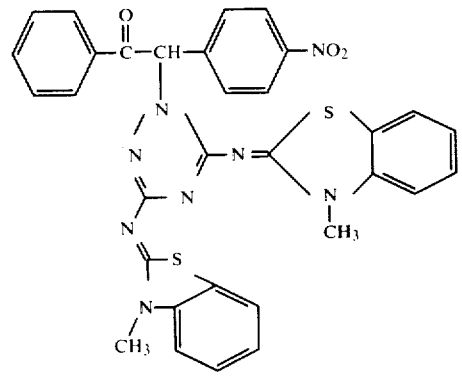
(24)

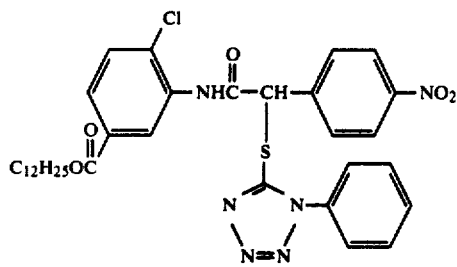

(25)

The compounds represented by the general formula (I) can be easily prepared by a method in which one hydrogen atom of the active methylene group of a compound having the general formula (V):

X—CH$_2$—R  (V)

wherein X and R have the same meaning as described in the general formula (I), is substituted with a halogen atom using conventional techniques, and the product is reacted with a compound of the formula

YH wherein Y has the same meaning as in formula (I) above, in the presence of a base in a conventional manner as described in British Pat. No. 1,331,179.

Further, of the compounds represented by the general formula (I), compounds in which Y is bonded through a sulfur atom can also be prepared by reacting a compound having the general formula (V) with a sulfenyl chloride which is obtained by reacting a compound of the formula YH with chlorine gas or sulfuryl chloride.

More specifically, of the compounds represented by the general formula (V), compounds in which X represents a

group wherein R$_1$ has the same meaning as in formula (I) above can be prepared as described in Wagner and Zook: *Synthetic Organic Chemistry* pp. 317 Method 178 and pp. 336 Method 193, John Willey & Sons, New York (1953). Compounds in which X represents a

group, a

group or a

group wherein R$_1$ has the same meaning as in formula (I) above can be prepared by converting the corresponding commercially available carboxylic acid to the corresponding carboxylic acid chloride and processing same as described in Wagner and Zook ibid. pp. 566 Method 348. Compounds in which X represents an —SO$_2$R$_1$ group wherein R$_1$ has the same meaning as in formula (I) above can be prepared as described in Wagner and Zook ibid. pp. 801 Method 529 using the corresponding sulfides prepared as described in Wagner and Zook ibid. pp. 787 Method 515. Compounds in which X represents an —SO$_2$OR$_1$ group wherein R$_1$ has the same meaning as in formula (I) above can be prepared as described in Wagner and Zook ibid. pp. 823 Method 552 using the corresponding sulfonyl chlorides. Compounds in which X represents an —SO$_2$NH$_2$ group, an —SO$_2$NHR$_1$ group or an —SO$_2$N(R$_1$)$_2$ group can be prepared as described in Wagner and Zook ibid. pp. 822 Method 551 using the corresponding sulfonyl chlorides. Compounds in which X represents a —CN group can be prepared as described in Wagner and Zook ibid. pp. 596 Method 384 after converting the corresponding carboxylic acids to the primary amides thereof. Compounds in which X represents an —N(R$_1$)$_3$ group wherein R$_1$ has the same meaning as in formula (I) above can be prepared in a conventional manner by way of tertiary amines. Compounds in which X represents a —COOR$_1$ group wherein R$_1$ has the same meaning as in formula (I) above can be prepared by esterifying the corresponding carboxylic acids in a conventional manner. Compounds represented by the general formula YH can be prepared in a conventional manner.

Typical methods for preparation of the compounds according to the present invention are illustrated below. Other compounds can also be prepared in a manner similar to these methods. Unless otherwise indicated herein, all parts, percents, ratios and the like are by weight.

SYNTHESIS EXAMPLE 1

Preparation of Compound (1)

p-Nitrophenyl acetyl chloride which was obtained from 80 g (0.44 mol) of p-nitrophenyl acetic acid and 80 g (0.66 mol) of thionyl chloride and 118 g (0.4 mol) of n-tetradecyloxybenzene was dissolved in 600 cc of carbon disulfide and to the solution 53 g of aluminum chloride was added at room temperature (about 20°–30° C.) with stirring for about 30 min. The mixture was refluxed with heating for 3 hours and carbon disulfide was distilled off under reduced pressure. The residue was added to a mixture of 400 g of ice, 600 cc of water and 30 cc of concentrated hydrochloric acid (12 N) and the crystals deposited were collected by filtration and recrystallized from a solvent mixture of ethanol and ethyl acetate (1:2 by vol) to obtain 156 g of p-n-tetradecyloxy-ω-(p-nitrophenyl)acetophenone. Yield: 86%, Melting Point: 84° to 85° C.

80 g (0.18 mol) of p-n-tetradecyloxy-ω-(p-nitrophenyl)acetophenone prepared as described above was dissolved in 400 cc of chloroform and to the solution 28 g (0.18 mol) of bromine dissolved in 50 cc of chloroform was gradually added dropwise while refluxing with heating. The mixture was washed with water and dried with anhydrous sodium sulfate. Chloroform was distilled off under reduced pressure and 91 g of p-n-tetradecyloxy-ω-bromo-ω-(p-nitrophenyl)acetophenone was obtained after recrystallization from n-hexane. Yield: 95%, Melting Point: 55° to 56° C.

30 g (0.54 mol) of p-n-tetradecyloxy-ω-bromo-ω-(p-nitrophenyl)acetophenone thus obtained and 24 g (0.084 mol) of 5-(3-methyl-2-benzothiazolinylidene)-aminobenzotriazole were dissolved in 100 cc of dimethylformamide and to the solution 11.2 g (0.11 mol) of triethylamine was added dropwise at room temperature. After stirring for 3 hours, 300 ml of water and 20 ml of concentrated hydrochloric acid (12 N) was added to the reaction solution and the solid deposited was removed by filtration. The chloroform layer of the filtrate was washed twice with water and the chloroform was distilled off under reduced pressure. The oily product residue was dissolved in a solvent mixture of acetonitrile and chloroform (2:1 by vol) by heating and the solution was cooled to room temperature. The crystals deposited were collected by filtration to obtain 36 g of Compound (1). Yield: 90%, Melting Point: 131° to 133° C.

SYNTHESIS EXAMPLE 2

Preparation of Compound (4)

8 g (0.014 mol) of p-n-tetradecyloxy-ω-bromo-ω-(p-nitrophenyl)acetophenone which was obtained as described in Synthesis Example 1 above and 2.4 g (0.014 mol) of 1-phenyl-5-mercaptotetrazole were dissolved in 100 cc of acetonitrile and to the solution 3.0 g (0.03 mol) of triethylamine was added at room temperature with stirring. After stirring for one hour, acetonitrile was distilled off under reduced pressure and to the oily product residue ethanol was added. The crystals deposited were collected by filtration and recrystallized from ethanol to obtain 8.4 g of p-n-octadecyloxy-ω-(1-phenyl-5-tetrazolylthio)-ω-(p-nitrophenyl)acetophenone. Yield: 95%, Melting Point: 82° to 95° C.

The non-color forming coupling compounds of the present invention can be incorporated into a photographic emulsion layer using known dispersion methods. For example, the method described hereinafter can be used.

The non-color forming coupling compound of the present invention can be advantageously mixed with a solvent dispersion by dissolving the coupling into either a water-immiscible organic solvent having a high boiling point (higher than about 170° C.), an organic solvent having a low boiling point or a water-soluble organic solvent, or into a mixture of such a water-immiscible organic solvent with a high boiling point and/or such as organic solvent with a low boiling point and/or such a water-soluble organic solvent.

All water-immiscible organic solvents having high boiling points as disclosed in U.S. Pat. No. 2,322,027 can be employed as solvents for the above-described purpose. Preferred examples of such solvents include di-n-butyl phthalate, benzylphthalate, triphenyl phosphate, tri-o-cresyl phosphate, diphenyl mono-p-tert-butylphenyl phosphate, dioctyl phthalate, dibutyl sebacate, acetyl tributyl citrate, tri-tert-octyltrimellitate, n-nonylphenol, dioctylbutyl phosphate, N,N-diethyllaurylamide, 3-pentadecylphenyl ethyl ether, 2,5-di-sec-amylphenyl butyl ether, and the like.

Suitable examples of organic solvents having a low boiling point (lower than about 170° C.) or water-soluble organic solvents which can be employed together with or instead of the above-described solvents having a high boiling point which can be used are described in U.S. Pat. Nos. 2,801,171; 2,801,170; 2,949,360 and the like.

In order to disperse the non-color forming coupling compounds of the present invention, a homogenizer for emulsification, a colloid mill, an ultrasonic emulsifying apparatus and the like can be usefully employed.

The non-color forming coupling compounds of the present invention may be used individually or as a combination of two or more thereof, or can be employed together with known two equivalent and/or four equivalent couplers.

Typical couplers which can be used are illustrated below, but the present invention should not be construed as being limited thereto. Illustrative yellow couplers include α-pivaloyl-α-(2,4-dioxo-5,5-dimethyl-3-oxazolidinyl)-2-chloro-5-[α-(2,4-di-tert-amylphenoxy)-butyramido]acetanilide, α-{m-[α-(2,4-di-tert-amylphenoxy)butyramido]}-benzoyl-2-methoxyacetanilide, α-p-methoxybenzoyl-α-(1-benzyl-5-ethoxy-2,4-dioxoimidazolidin-3-yl)-2-chloro-5-[α-(2,4-di-tert-amylphenoxy)butyramido]acetanilide,α-pivaloyl-α-(1-benzyl-5-ethoxy-2,4-dioxoimidazolidin-3-yl)-2-chloro-5-hexadecylsulfonamidoacetanilide, etc. Suitable magenta couplers are 1-(2,4,6-trichlorophenyl)-3-{3-[α-(2,4-di-tert-amylphenoxy)acetamido]-benzamido}-5-pyrazolone, 1-(2,4,6-trichlorophenyl)-3-(2-chloro-5-tetradecanamido)anilino-5-pyrazolone, etc. Examples of cyan couplers are 1-hydroxy-2-N-[γ-(2,4-di-tert-amylphenoxy)propyl]naphthamide, 4,6-dichloro-5-methyl-2-[α-(2,4-di-tert-amylphenoxy)-butyramido]phenol, 2-heptafluorobutyramido-5-[α-(2,4-di-tert-amylphenoxy)acetamido]phenol, 2-(2,2,3,4,4,4-hexafluorobutyramido)-5-[α-(2,4-di-tert-amylphenoxy)-butyramido]phenol, etc.

Moreover, the coupling compounds of the present invention can also be used in combination with colored couplers instead of DIR couplers as disclosed in U.S. Pat. No. 3,703,375. These coupling compounds may be mixed in the same dispersed droplet or each of these coupling compounds can be dispersed separately.

The amount of the non-color forming coupling compound employed in the practice of the present invention can be varied over a wide range depending on the type of light-sensitive material or processing used. When the coupling compound of this invention is incorporated in a light-sensitive material, the coupling compound can be effectively employed in an amount of particularly from about 0.0005 to about 0.5 mol per mol of the silver halide present in the emulsion. On the other hand, when the coupling compound of this invention is added to a developer solution, the coupling compound may be effectively employed in an amount of particularly from about $1 \times 10^4$ mol to about $1 \times 10^{-1}$ mol per 1,000 ml of the developer solution.

The non-color forming coupling compound of the present invention can be used in multilayer color light-sensitive materials having a superposed layer structure as disclosed in U.S. Pat. No. 3,726,681, British Pat. Nos. 818,687 and 923,045, U.S. Pat. No. 3,516,831, Japanese Patent Applications Nos. 5179/1975 and 81142/1976, etc. Further, the coupling compound of the present invention can be used together with or instead of DIR couplers according to the method disclosed in German Patent Application (OLS) No. 2,322,165.

The non-color forming coupling compound of the present invention can be used together with DIR hydroquinones as described in U.S. Pat. No. 3,379,529; Japanese Patent Application (OPI) No. 129536/1974, etc.

The silver halide emulsion which can be used in the present invention includes those of silver chloride and silver bromide and also a mixed silver halide such as silver chlorobromide, silver iodobromide, silver chloroiodobromide, etc.

The silver halide emulsion can be produced using known conventional methods, for example, a single or double jet method, a controlled double jet method, etc.

Furthermore, silver halide grains wherein latent images are formed in the surface portion thereof or those wherein latent images are formed in the interior portion thereof can be used.

The silver halide emulsion is preferably sensitized with a known chemical sensitizer, for example, sodium thiosulfate N,N,N'-trimethyl thiourea, aurous thiocyanate complex salt, aurous thiosulfate complex salt, stannous chloride, hexamethylenetetramine, etc.

The silver halide grains can be fogged with a reducing agent such as hydrazine or a combination of a reducing agent and a gold compound or a labile sulfur compound.

The photographic emulsion used in the color photographic light-sensitive material according to the present invention can be spectrally sensitized to be sensitive to blue, green or red light using a cyanine dye such as a cyanine, merocyanine or carbocyanine dye, individually or in combination, or using a combination of these dyes and a styryl dye, amino stilbene compound or the like, it desired.

Known stabilizing agents and anti-fogging agents, for example, 4-hydroxy-6-methyl-1,3,4a,7-tetrazaindene, 3-methylbenzothiazole, 1-phenyl-5-mercaptotetrazole, a mercapto compound, a metal salt, etc., can be used in the photographic emulsion.

The formation of dye images can be achieved with various kinds of color photographic processing systems. One process comprises processing an image-wise exposed silver halide light-sensitive material with a color developer solution containing an aromatic primary amine color developing agent in which a coupler is dissolved to form a water-insoluble or diffusion resistant dye image in the emulsion layer, that is, a coupler-in-developer type color process. Another process comprises processing an image-wise exposed light-sensitive material having a silver halide emulsion layer containing a diffusion resistant coupler with a color developer solution containing an aromatic primary amine color developing agent to form a water-insoluble or diffusion resistant dye image in the emulsion layer. Still another process comprises processing an image-wise exposed light-sensitive photographic material having a silver halide emulsion layer in combination with a diffusion resistant coupler with an alkaline developer solution containing an aromatic primary amine color developing agent to form a diffusible dye which diffuses into an image receiving layer containing a hydrophilic colloid, that is, a diffusion transfer process.

The couplers can be dispersed in the photographic emulsion after dissolving them in an aqueous medium or an organic solvent.

Oil-soluble diffusion resistant couplers which are suitable for use in a coupler-in-emulsion type system are advantageously dispersed in a photographic emulsion as a solution in an organic solvent. Specific examples of processes for dispersing the coupler are described in detail in U.S. Pat. No. 3,676,131. Suitable organic solvents for dissolving the coupler are those which are slightly soluble in water and have a high boiling point and including, for example, a substituted hydrocarbon, a carboxylic acid ester, a benzoic acid ester, a citric acid ester, a carboxylic acid amide and a phosphoric acid ester. Specific examples of such compounds are di-n-butyl phthalate, n-octyl benzoate, o-acetyltributyl citrate, tricresylphosphate, tri-n-hexylphosphate, N,N-diethylcaprylamide, and the like. In addition to these high boiling point solvents, it is advantageous to use an auxiliary solvent having a low boiling point in order to assist the dissolution of the couplers. Examples of such compounds are propylene carbonate, ethyl acetate, butyl acetate, cyclohexanol, tetrahydrofuran, cyclohexanone, etc.

It is advantageous to use a surface active agent to aid in finely dispersing the solvents in a hydrophilic colloid used for a photographic emulsion. Diffusion resistant couplers having a carboxylic acid group or a sulfonic acid group together with a ballast group in the molecule are soluble in a neutral or weakly alkaline aqueous solution. The aqueous solution can be added to a photographic emulsion.

The couplers are generally incorporated into the light-sensitive material in the amount of about 10 to about 1,500 g per mol of silver halide and employed in a developer solution in an amount of about 0.2 to about 50 g/l, preferably 0.5 to 10 g/l. However, the amount can be varied depending on the purpose of use.

The couplers can be employed in various silver halide light-sensitive materials, for example, color negative films, color positive films, color reversal films, color papers, and various other color light-sensitive materials. In addition, the couplers can be employed in color direct positive light-sensitive materials, instant color light-sensitive materials such as those for a color diffusion transfer process, etc.

The couplers can be used in a known multilayer structure of a multilayer color light-sensitive material, for example, those described in U.S. Pat. Nos. 3,726,681 and 3,516,831, British Pat. Nos. 818,687 and 923,045, a method described in Japanese Patent Application No. 5179/1975, and a method in which the coupler is used together with a DIR compound as described in German Patent Application (OLS) No. 2,322,165 and U.S. Pat. No. 3,703,375.

To increase the stability of the color photographic images formed it is advantageous for the light-sensitive material to contain a p-substituted phenol derivative, e.g., a hydroquinone derivative, in an emulsion layer thereof or an adjacent layer thereto. Particularly preferred p-substituted phenol derivatives are those described in U.S. Pat. Nos. 2,360,290, 2,418,613, 2,675,314, 2,710,801, 2,728,659, 2,732,300, 2,735,765, 2,816,028, 3,457,079 and 3,069,262, Japanese Patent Publication No. 13496/1968, U.S. Pat. No. 2,735,765, Japanese Patent Application (OPI) No. 4738/1972, U.S. Pat. Nos. 3,432,300, 3,573,050, 3,574,627 and 3,764,337.

The light-sensitive material containing the couplers can contain an ultraviolet absorbing agent as described, for example, in U.S. Pat. Nos. 3,250,617 and 3,253,921 in an emulsion layer or an adjacent layer thereto so as to stabilize the images formed.

The support for the light-sensitive material of the present invention can be a cellulose acetate film, a cellulose acetate butyrate film, a polystyrene film, a polyethylene terephthalate film, a laminate of these films, a glass, a paper, a baryta paper, a paper coated or laminated with baryta or a polymer of an α-olefin having 2 to 10 carbon atoms, such as polyethylene, polypropylene, an ethylene-butene copolymer, etc. A suitable coating amount of silver halide per unit area of the support is about $1 \times 10^{-4}$ to about $10^{-2}$ mol/m².

The photographic light-sensitive material can be usually processed, after exposure, employing known methods including basically a color development step, a bleaching step and a fixing step. Each step can be conducted separately or two or more steps can be carried out as one step using a processing solution which has the capability of performing each of these steps. For example, the use of a bleach-fixing solution is one example of such a combination. If desired, the processing can include other steps such as a prehardening, a neutralization, a first development (black-and-white development), an image stabilizing, a water washing, etc.

The processing temperature used sometimes is below about 18° C. but often advantageously is above about 18° C. In particular, the temperature generally ranges from about 20° to about 60° C.

A color developer solution is an alkaline aqueous solution having a pH of 8 or above, and particularly 9 to 12, which contains a color developing agent.

Preferred examples of the above described color developing agents are 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-3-methyl-N-ethyl-N-β-methoxyethylaniline, etc. In addition, the compounds described in U.S. Pat. Nos. 2,193,015 and 2,592,364, Japanese Patent Application (OPI) No. 64933/1973 and L. F. A. Mason, *Photographic Processing Chemistry*, pages 226 to 229, Focal Press, London (1966), can be also used.

The light-sensitive material containing the coupling compound of the present invention can be developed in a color development step even in the presence of a competing coupler without practical problems arising.

After the color development step, the light-sensitive material of the present invention is subjected to a bleaching in a conventional manner. The bleaching can be carried out separately or simultaneously with fixing. In the latter case, a fixing agent is added to a bleaching solution to make a bleach-fixing bath. Many compounds can be used as a bleaching agent. For example, a ferricyanide, a bichromate, a complex salt of a polyvalent metal cation such as iron (III), cobalt (III), etc., and an organic acid, for example, a metal complex salt of an aminopolycarboxylic acid such as ethylenediamine tetraacetic acid, nitrilotriacetic acid, diaminopropanol tetraacetic acid, etc., citric acid, tartaric acid, malic acid, etc., can be used. It is possible to add to this processing solution a bleaching accelerating agent as described in U.S. Pat. Nos. 3,042,520 and 3,241,966, Japanese Patent Publication Nos. 8506/1970 and 8836/1970, etc., and various other additives.

The present invention can be used for light-sensitive materials having a low silver content wherein the amount of silver halide in the emulsion is from about one half to about one hundredth of that in conventional light-sensitive materials. It is possible to obtain a satisfactory color image in such color light-sensitive materials having a low silver halide content by applying an image forming process which comprises a color intensification using a peroxide, a cobalt complex salt or sodium chlorite, for example as described in German Patent Application (OLS) No. 2,357,694, U.S. Pat. Nos. 3,674,490 and 3,761,265, German Patent Application (OLS) No. 2,044,833, 2,056,359, 2,056,360, 2,226,770, Japanese Patent Application (OPI) Nos. 9728/1973 and 9729/1973, etc.

The present invention will be further illustrated by reference to the following examples, but the present invention should not be construed as being limited to the following examples.

EXAMPLE 1

Samples were prepared in the following manner.

Sample 101

On a transparent cellulose triacetate film support were coated the following First Layer to Fourth Layer in this order and dried to prepare a sample. The composition and method of preparation of the coating solution used for each layer was as follows.

First Layer: Red-Sensitive Emulsion Layer 1 kg of a high speed silver iodobromide emulsion (silver content: 0.6 mol, iodide content: 6 mol%) was spectrally sensitized using $4 \times 10^{-5}$ mol of Sensitizing Dye I and $1 \times 10^{-5}$ of Sensitizing Dye II per mol of silver, respectively. 550 g of Dispersion I prepared by dissolving 100 g of Coupler A into 100 cc of tricresyl phosphate and 200 cc of ethyl acetate, and then dispersing the resulting solution into 1 kg of a 10% aqueous gelatin solution using 4 g of sodium nonylbenzenesulfonate (surface active agent) was added to the spectrally sensitized silver iodobromide emulsion and the mixture was stirred. To the mixture an aqueous solution of 2 g of sodium 2,4-dichloro-6-hydroxytriazine was added as a hardener. The thus-prepared coating solution was coated on a transparent cellulose triacetate film support in a silver coated amount of 2.0 g/m².

Second Layer: Intermediate Layer 50 g of 2,5-di-tert-octylhydroquinone was dissolved in 100 cc of tricresyl phosphate and dispersed in 1 kg of a 10% aqueous gelatin solution in the same manner as described for Dispersion I. 250 g of thus prepared dispersion and an aqueous solution of 2 g of sodium 2,4-dichloro-6-hydroxytriazine were added to 1 kg of a 10% aqueous gelatin solution and the mixture stirred. The coating solution was coated in a dry thickness of 1.5 microns.

Third Layer: Green-Sensitive Emulsion Layer 1 kg of a high speed silver iodobromide emulsion (same as described for the First Layer) was spectrally sensitized using $3 \times 10^{-5}$ mol of Sensitizing Dye III and $1 \times 10^{-5}$ mol of Sensitizing Dye IV per mol of silver, respectively. Using 100 g of Coupler B, Dispersion II was prepared in the same manner as described for Dispersion I. 700 g of Dispersion II was added to the spectrally sensitized silver iodobromide emulsion and an aqueous solution of 2 g of sodium 2,4-dichloro-6-hydroxytriazine was added thereto with stirring. The coating solution was coated in a silver coated amount of 1.5 g/m².

Fourth Layer: Protective Layer

To 1 kg of a 10% aqueous gelatin solution was added 2 g of sodium 2,4-dichloro-6-hydroxytriazine. The solution was coated in a dry thickness of 1.5 microns.

Samples 102 to 105

Samples 102 to 105 were prepared in the same manner as described for Sample 101 except that the optimum amount of non-color forming coupling compound (as shown in Table 1 below) was additionally incorporated into the coupler solvent in Dispersion II used in the Third Layer of Sample 101.

The compounds used for the preparation of the above-described samples were:

Sensitizing Dye I: Pyridinium salt of anhydro-5,5'-dichloro-3,3'-disulfopropyl-9-ethylthiacarbocyanine hydroxide Sensitizing Dye II: Triethylamine salt of anhydro-9-ethyl-3,3'-di-(3-sulfopropyl)-4,5,4',5'-dibenzothiacarbocyanine hydroxide Sensitizing Dye III: Sodium salt of anhydro-9-ethyl-5,5'-dichloro-3,3'-disulfopropyloxacarbocyanine Sensitizing Dye IV: Sodium salt of anhydro-5,6,5',6'-tetrachloro-1,1'-diethyl-3,3'-disulfopropoxyethoxyethylimidazolocarbocyanine hydroxide Coupler A: 1-Hydroxy-N-[γ-(2,4-di-tert-amylphenoxy)propyl]-2-naphthamide Coupler B: 1-(2,4,6-Trichlorophenyl)-3-[3-(2,4-di-tert-amylphenoxyacetamido)benzamido]-5-pyrazolone (4-equivalent coupler)

Comparative DIR Coupler D-1: p-n-Tetradecyloxy-ω-phenyl-ω-[5- or 6-(3-methylbenzothiazolinyliden)-aminobenzotriazolyl)]acetophenone.

Samples 101 to 105 were exposed stepwise using green light (20 CMS) for 1/100 second and then exposed uniformly using red light (20 CMS) for 1/100 second, and subjected to the following processing steps at 38° C. In addition, these samples were line image exposed to soft X-rays (20 CMS) for 1/100 second through a slit with a 4 mm width and a slit with a 10 μm width and subjected to the same processing as above.

| 1. Color Development | 3 min 15 sec |
|---|---|
| 2. Bleaching | 6 min 30 sec |
| 3. Washing | 3 min 15 sec |
| 4. Fixing | 6 min 30 sec |
| 5. Washing | 3 min 15 sec |
| 6. Stabilizing | 3 min 15 sec |

The processing solutions used in the above steps had the following compositions:

| Color Developer Solution | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N-Ethyl-N-β-hydroxyethylamino)-2-methylaniline Sulfate | 4.5 g |
| Water to make | 1 liter |
| Bleaching Solution | |
| Ammonium Bromide | 160.0 g |
| Ammonia (28% aq. soln.) | 25.0 ml |
| Sodium Ferric Ethylenediaminetetraacetate | 130 g |
| Glacial Acetic Acid | 14 ml |
| Water of make | 1 liter |
| Fixing Solution | |
| Sodium Tetrapolyphosphate | 2.0 g |
| Sodium Sulfite | 4.0 g |
| Ammonium Thiosulfate (70% aq. soln.) | 17.0 ml |
| Sodium Bisulfite | 4.6 g |
| Water to make | 1 liter |
| Stabilizing Solution | |
| Formaldehyde | 8.0 ml |
| Water to make | 1 liter |

In the characteristic curve thus obtained, when the gradation of the curve of the red filter optical density vs. log (exposure amount) (which corresponds to the First Layer) is desginated $\gamma_R$ and the gradation of the curve of the green filter optical density vs. log (exposure amount) (which corresponds to the Third Layer) is designated $\gamma_G$, the value of $\gamma_R/\gamma_G$ is considered to be the amount of interlayer effects from the Third Layer to the First Layer ($\gamma_G$ values of the samples other than Sample 101 are substantially constant). That is, the value of $\gamma_R/\gamma_G$ is minus and larger numerical values mean larger interlayer effects from the Third Layer (green-sensitive layer) to the First Layer (red-sensitive layer). The $\gamma_R/\gamma_G$ value of each sample is shown in Table 1 below.

The optical density of each sample obtained by line image exposure to soft X-rays was measured by microdensitometer tracing with green light. When the density of the line image with a 10μ width is designated $D_1{}^G$ and the density of the line image with a 4 mm width is designated $D_2{}^G$, the value of $(D_1{}^G - D_2{}^G)/D_1{}^G$ means the amount of edge effects of the sample when the sample is observed with green light. That is, a larger value of $(D_1{}^G - D_2{}^G)/D_1{}^G$ means large edge effects when observed with green light. The value of $(D_1{}^G - D_2{}^G)/D_1{}^G$ of each sample is also shown in Table 1 below.

Furthermore, each sample was exposed stepwise with white light (20 CMS) for 1/100 second and processed in the same manner as described above and then the graininess of the color image thereof was measured using the conventional RMS (Root Mean Square) method using green light. The results of the RMS graininess at densities of 0.5 and 1.5 are also shown in Table 1 below.

Table 1

| Sample No. | Non-Color Forming Coupling Compound | | $\gamma_G$ | Inter-Image Effects ($\gamma_R/\gamma_G$) | Edge Effects ($D_1G - D_2G)/D_1G$ | RMS Graininess** | |
|---|---|---|---|---|---|---|---|
| | Compound | Amount* (mol%) | | | | $D_G = 0.5$ | $D_G = 1.5$ |
| Control | | | | | | | |
| 101 | — | — | 1.47 | 0.07 | 0.02 | 0.053 | 0.075 |
| Present Invention | | | | | | | |
| 102 | Compound (1) | 6 | 0.84 | −0.31 | 0.31 | 0.040 | 0.052 |
| 103 | Compound (6) | 8 | 0.85 | −0.27 | 0.25 | 0.041 | 0.054 |

Table 1-continued

| Sample No. | Non-Color Forming Coupling Compound Compound | Amount* (mol%) | $\gamma_G$ | Inter-Image Effects $(\gamma_R/\gamma_G)$ | Edge Effects $(D_1G - D_2G)/D_1G$ | RMS Graininess** $D_G = 0.5$ | $D_G = 1.5$ |
|---|---|---|---|---|---|---|---|
| 104 Comparison | Compound (10) | 7 | 0.89 | −0.30 | 0.28 | 0.038 | 0.050 |
| 105 | DIR Coupler (D-1) | 22 | 0.87 | −.015 | 0.15 | 0.048 | 0.068 |

*Amount: mol% to Coupler B.
**RMS Graininess: measured with a slit of 10 μ × 10 μ.
The smaller the numerical value in Table 1 the better the graininess.

From the results shown above it is apparent that Compounds (1), (6) and (10) of the present invention provide larger interlayer effects, edge effects and effects of reducing the graininess of the color image in comparison with the Comparison DIR Coupler D-1 even though the amount of the compounds of the present invention is smaller than the comparison compound.

EXAMPLE 2

Samples were prepared in the following manner.

Samples 201 to 204

Samples 201 to 204 were prepared in the same manner as Sample 105 of Example 1 except that Compound (4) of the present invention and Comparison Non-Color Forming DIR Couplers D-2, D-3 and D-4 were used in the amount shown in Table 2, respectively, in place of Non-Color Forming DIR Coupler D-1 added to the Third Layer of Sample 105.

Samples 102 to 105 prepared as described in Example 1 were also used in this example.

The compounds used for the preparation of the above described samples were:

Comparison Non-Color Forming DIR Coupler D-2: p-Tetradecyloxy-ω-bromo-ω-(1-phenyl-5-tetrazolylthio)acetophenone Comparison Non-Color Forming DIR Coupler D-3: p-Tetradecyloxy-ω-(1-phenyl-5-tetrazolylthio)acetophenone Comparison Non-Color Forming DIR Coupler D-4: p-Tetradexyloxy-ω-di-(1-phenyl-5-tetrazolylthio)acetophenone These samples were stored for 4 days either under room temperature conditions (20° C., 70% RH) or under conditions of high humidity and high temperature (40° C., 80% RH), and then they were exposed stepwise using white light (20 CMS) for 1/100 second and processed in the same manner as described in Example 1. The optical densities with green light and red light of the thus-processed samples were measured and the characteristic values obtained are shown in Table 2 below.

Table 2

| | Non-Color Forming Coupling Compound | | Relative Sensitivity on Storage at Room Temperature | | Relative Sensitivity on Storage at 40° C., 80% RH | |
|---|---|---|---|---|---|---|
| Sample No. | Compound | Amount (mol%) | Green Light | Red Light | Green Light | Red Light |
| Present Invention | | | | | | |
| 102 | Compound (1) | 6 | 100 | 100 | 98 | 97 |
| 103 | Compound (6) | 8 | 98 | 99 | 99 | 97 |
| 104 | Compound (10) | 7 | 99 | 98 | 96 | 98 |
| 201 | Compound (4) | 6 | 99 | 100 | 98 | 99 |
| Comparison | | | | | | |
| 105 | DIR Coupler D-1 | 22 | 98 | 99 | 88 | 94 |
| 202 | DIR Coupler D-2 | 35 | 99 | 97 | 73 | 89 |
| 203 | DIR Coupler D-3 | 35 | 99 | 98 | 70 | 92 |
| 204 | DIR Coupler D-4 | 31 | 96 | 95 | 67 | 83 |

Amount: mol% to Coupler B.

From the results described above, it is apparent that Compounds (1), (6), (10) and (4) of the present invention act to reduce the sensitivity of the layer to which the compounds are added or the emulsion layer adjacent thereto to a markedly lesser extent in comparison with Comparison Non-Color Forming DIR Couplers D-1, D-2, D-3 and D-4 under storage at high humidity and high temperature. This illustrates that the compounds of the present invention are extremely stable in comparison with the above-described comparison non-color forming DIR Couplers compounds.

EXAMPLE 3

On a cellulose triacetate film support were coated layers having the compositions set forth below to prepare a multilayer color light-sensitive material. The compounds indicated by an asterisk are the same compounds as described in Example 1.

First Layer: Antihalation Layer (AHL)

A gelatin layer of 3 mμ thick containing black colloidal silver (30 mg/m²)

Second Layer: Intermediate Layer (ML)

A gelatin layer of 2 mμ thick containing a dispersion of 2,5-di-tert-octylhydroquinone Third Layer: First Red-Sensitive Emulsion Layer (RL$_1$)

A silver iodobromide emulsion (iodide content: 4 mol%)
silver coated amount: 1.82 g/m²
Sensitizing Dye I*    $6 \times 10^{-5}$ mol per mol of silver
Sensitizing Dye II*    $1.5 \times 10^{-5}$ mol per mol of silver
Coupler A*    0.04 mol per mol of silver
Coupler C-1    0.0015 mol per mol of silver tively. The amount of the Non-Color Forming DIR Couplers used are shown in Table 3.

Table 3

| Layer Added | Sample 301 | | Sample 302 | | Sample 303 | | Sample 304 | |
|---|---|---|---|---|---|---|---|---|
| | Compound | Amount | Compound | Amount | Compound | Amount | Compound | Amount |
| $RL_1$ | Compound (3) | 0.0015 | Compound (10) | 0.002 | DIR Coupler D-3 | 0.009 | DIR Coupler D-1 | 0.005 |
| $RL_2$ | " | 0.00015 | " | 0.0002 | " | 0.009 | " | 0.0005 |
| $GL_1$ | " | 0.003 | " | 0.003 | " | 0.015 | " | 0.009 |
| $GL_2$ | " | 0.0008 | " | 0.001 | " | 0.003 | " | 0.002 |
| $BL_1$ | " | 0.002 | " | 0.003 | " | 0.008 | " | 0.005 |

Amount: mol per mol of silver

—continued

| | |
|---|---|
| Coupler C-2 | 0.0015 mol per mol of silver |
| Compound (3) | 0.0015 mol per mol of silver |

Fourth Layer: Second Red-Sensitive Emulsion Layer ($RL_2$)

A silver iodobromide emulsion (iodide content: 4 mol%)
silver coated amount: 1.4 g/m²

| | |
|---|---|
| Sensitizing Dye I* | $3 \times 10^{-5}$ mol per mol of silver |
| Sensitizing Dye II* | $1.2 \times 10^{-5}$ mol per mol of silver |
| Coupler A* | 0.005 mol per mol of silver |
| Coupler C-1 | 0.0008 mol per mol of silver |
| Coupler C-2 | 0.0008 mol per mol of silver |
| Coupler C-3 | 0.015 mol per mol of silver |
| Compound (3) | 0.00015 mol per mol of silver |

Fifth Layer: Intermediate Layer (ML)
Same as the Second Layer

Sixth Layer: First Green-Sensitive Emulsion Layer ($GL_1$)

A silver iodobromide emulsion (iodide content: 4 mol%)
silver coated amount: 1.55 g/m²

| | |
|---|---|
| Sensitizing Dye III* | $3 \times 10^{-5}$ mol per mol of silver |
| Sensitizing Dye IV* | $1 \times 10^{-5}$ mol per mol of silver |
| Coupler B* | 0.05 mol per mol of silver |
| Coupler M-1 | 0.008 mol per mol of silver |
| Compound (3) | 0.003 mol per mol of silver |

Seventh Layer: Second Green-Sensitive Emulsion Layer ($GL_2$)

A silver iodobromide emulsion (iodide content: 4 mol%)
silver coated amount: 1.7 g/m²

| | |
|---|---|
| Sensitizing Dye III* | $2.5 \times 10^{-5}$ mol per mol of silver |
| Sensitizing Dye IV* | $0.8 \times 10^{-5}$ mol per mol of silver |
| Coupler B* | 0.02 mol per mol of silver |
| Coupler M-1 | 0.003 mol per mol of silver |
| Compound (3) | 0.0008 mol per mol of silver |

Eighth Layer: Yellow Filter Layer (YEL)

A gelatin layer of 3 mμ thick containing yellow colloidal silver (300 mg/m²) and a dispersion of 2,5-di-tert-octylhydroquinone Ninth Layer: First Blue-Sensitive Emulsion Layer ($BL_1$)

A silver iodobromide emulsion (iodide content: 5 mol%)
silver coated amount: 1.55 g/m²

| | |
|---|---|
| Coupler Y-1 | 0.25 mol per mol of silver |
| Compound (3) | 0.002 mol per mol of silver |

Tenth Layer: Second Blue-Sensitive Emulsion Layer ($BL_2$)

A silver iodobromide emulsion (iodide content: 5 mol%)
silver coated amount: 1.2 g/m²

| | |
|---|---|
| Coupler Y-1 | 0.06 mol per mol of silver |

Eleventh Layer: Protective Layer (PL)

A gelatin layer containing an ultra-fine grain silver iodobromide emulsion (containing 0.06 mol of silver per kg of emulsion, having an iodide content of 1.4 mol%, and having an average grain size of 0.03 μ), and polymethyl methacrylate particles (250 mg/m²) (having a diameter of about 1.5 μ)
silver coated amount: 2.3 g/m²

A gelatin hardener and a surface active agent as described in Example 1 were incorporated into each of the layers in addition to the above-described components.

The thus-prepared sample was designated Sample 301.

Samples 302 to 304

Samples 302 to 304 were prepared in the same manner as Sample 301 except that Compound (10), Comparison Non-Color Forming DIR Coupler D-3 and Comparison Non-Color Forming DIR Coupler D-1 were used in place of Compound (3) of Sample 301, respectively. The amount of the Non-Color Forming DIR Couplers used are shown in Table 3.

The couplers used for the preparation of these samples were as follows.

Coupler C-1: 1-Hydroxy-4-[2-(2-hexadecyloxycarbonyl)-phenylazo]-2-[N-(1-naphthyl)]naphthamide Coupler C-2: 1-Hydroxy-4-[4-(ethoxycarbonyl)-phenylazo]-2-(N-dodecyl)naphthamide Coupler C-3: 1-Hydroxy-4-iodo-2-(N-dodecyl)naphthamide Coupler M-1: 1-(2,4,6-Trichlorophenyl)-3-hexadecanamido-4-(4-hydroxyphenyl)azo-5-pyrazolone Coupler Y-1: α-(2,4-Dioxo-5,5-dimethyloxazolidinyl)-α-pivaloyl-2-chloro-5-[α-(2,4-di-tert-amylphenoxy)-butyramido]acetanilide The samples thus prepared were exposed stepwise with white light (20 CMS) for 1/100 second and subjected to sensitometry as described in Example 1. The sensitivity and gradation in each emulsion layer of Samples 301 to 304 were approximately equal.

Evaluations of the edge effects and the interlayer effects of these samples were carried out in the same manner as described in Example 1. The results obtained are shown in Table 4 below.

Table 4

| Sample No. | Measured Light | Edge Effects $(D_1-D_2)/D_1$ | Interimage Effects $(\gamma_R/\gamma_G)$ | $(\gamma_G/\gamma_R)$ |
|---|---|---|---|---|
| Present Invention | | | | |
| 301 | Blue Light | 0.32 | | |
| | Green Light | 0.39 | −0.36 | −0.33 |
| | Red Light | 0.41 | | |
| 302 | Blue Light | 0.28 | | |
| | Green Light | 0.31 | −0.30 | −0.27 |
| | Red Light | 0.38 | | |
| Comparison | | | | |
| 303 | Blue Light | 0.08 | | |
| | Green Light | 0.09 | −0.05 | −0.07 |
| | Red Light | 0.11 | | |
| 304 | Blue Light | 0.15 | | |
| | Green Light | 0.15 | −0.15 | −0.13 |
| | Red Light | 0.20 | | |

It is apparent from the results shown above that Samples 301 and 302 which contain Compounds (3) and (10) of the present invention, respectively, show greater edge effects and interlayer effects as compared with Samples 303 and 304 which contain Comparison DIR Couplers D-3 and D-1; respectively, even though the amount of Compound (3) or (10) was smaller than that of Comparison DIR Coupler D-3 or D-1.

Furthermore, these samples were cut into films of 35 mm size and photographed to form negative films. Color prints were prepared by printing the negative films using an enlarging technique. The color prints obtained using Samples 301 and 302 had a fine graininess and a sharp image and showed clear colors, particularly clearly reproducing green and red colors in comparison with those obtained using Samples 303 and 304.

These results indicated that Compounds (3) and (10) provided excellent characteristics in terms of improving graininess, sharpness and color reproduction.

EXAMPLE 4

Sample 401 having the layer structure as shown in FIG. 1 was prepared as follows. In a red-sensitive silver iodobromide emulsion (AgI; 7 mol%) which was spectrally sensitized using Sensitizing Dyes I and II described in Example 1, 1-hydroxy-4-chloro-2-n-dodecylnapththamide was emulsified and mixed as a cyan coupler. In a green-sensitive silver iodobromide emulsion (AgI: 4 mol%) which was spectrally sensitized using Sensitizing Dyes III and IV described in Example 1, 1-(2,4,6-trichlorophenyl)-3-[3-(2,4-di-tert-amylphenoxyacetamido)benzamido]-5-pyrazolone was emulsified and mixed as a magenta coupler. In a blue-sensitive silver iodobromide emulsion (AgI: 4 mol%), α-pivaloyl-α-[4-(4-benzyloxysulfonyl)phenoxy]-2-chloro-5-[γ-(2,4-di-tert-amylphenoxy)butyramido]acetanilide was emulsified and mixed as a yellow coupler. These emulsions were coated on a cellulose triacetate film support to prepare a color reversal photographic light-sensitive material Sample 401.

Additionally, in the emulsification of each coupler, dibutyl phthalate and tricresyl phosphate were used as a solvent for the couplers and sorbitan monolaurate and sodium dodecylbenzenesulfonate were used as an emulsifier.

With Sample 401, an antihalation layer containing black colloidal silver and a gelatin intermediate layer were provided under the red-sensitive emulsion layer, a filter layer of yellow colloidal silver was provided between the green-sensitive emulsion layer and the blue-sensitive emulsion layer, an intermediate layer comprising gelatin containing dispersed therein di-tert-amylhydroquinone was provided between the green-sensitive emulsion layer and the red-sensitive emulsion layer, and a protective layer mainly comprising gelatin was provided on the blue-sensitive emulsion layer.

A gelatin hardener and a surface active agent as described in Example 1 were added to each layer.

The coated silver amount of the red-sensitive emulsion layer was 1.5 g/m$^2$, that of the green-sensitive emulsion layer was 1.5 g/m$^2$, and that of the blue-sensitive emulsion layer was 0.9 g/m$^2$.

The molar ratios of silver/coupler in each emulsion layer were 8.0 in the red-sensitive emulsion layer, 9.5 in the green-sensitive emulsion layer and 5.0 in the blue-sensitive emulsion layer.

SAMPLES 402 to 404

Samples 402 to 404 were prepared in the same manner as Sample 401 except that the compounds shown in Table 5 were additionally dissolved in the coupler solvents used for the cyan coupler and the magenta coupler, emulsified, and added to the red-sensitive emulsion layer and the green sensitive emulsion layer, respectively, of Sample 401.

Samples 401 to 404 thus-prepared were stepwise exposed to red light and then uniformly exposed to green light (20 CMS) for 1/100 second so as to provide a color density of 70% of the maximum color density obtained by color development of the green-sensitive emulsion layer and subjected to the color reversal processing as shown below.

| Processing Step | Temperature (°C.) | Time (min) |
|---|---|---|
| First Development (black-and-white) | 30 | 5 |
| Stopping Bath | " | 1 |
| Washing | " | 2 |
| Fogging Bath | " | 2 |
| Color Develoment | " | 7 |
| Stopping Bath | " | 2 |
| Hardening Bath | " | 2 |
| Washing | " | 2 |
| Bleaching Bath | " | 4 |
| Washing | " | 2 |
| Fixing Bath | " | 4 |
| Washing | " | 2 |
| Drying | " | |

| Composition of the First Developer Solution | |
|---|---|
| Sodium Sulfite | 60.0 g |
| 1-Phenyl-3-pyrazolidone | 0.3 g |
| Hydroquinone | 5.0 g |
| Sodium Carbonate (monohydrate) | 41.0 g |
| Potassium Bromide | 2.0 g |
| Potassium Iodide (1% aq. soln.) | 1.0 ml |
| Potassium Thiocyanate (1N aq. soln.) | 10.0 ml |
| Sodium Hydroxide (10% aq. soln.) | 2.0 ml |
| Water to make | 1 liter |

| Composition of Stopping Solution | |
|---|---|
| Sodium Acetate | 30 g |
| Glacial Acetic Acid | 8 ml |
| Water to make | 1 liter |

| Composition of Fogging Bath | |
|---|---|
| Sodium Hydroxide | 2.0 g |
| Sodium Borohydride | 0.1 g |
| Water to make | 1 liter |

| Composition of Color Developer Solution | |
|---|---|
| Benzyl Alcohol | 5.0 ml |
| Sodium Hydroxide | 0.5 g |
| Diethylene Glycol | 3.0 me |
| Sodium Hexametaphosphate | 2.0 g |
| Sodium Sulfite | 2.0 g |
| Potassium Bromide | 2.0 g |
| 4-Amino-3-methyl-N-ethyl-β-hydroxyethylaniline Sesquisulfate (monohydrate) | 5.0 g |
| Citrazinic Acid | 0.4 g |
| Metaboric Acid | 0.5 g |
| Nabox (sodium metaborate) | 77.0 g |
| Water to make | 1 liter |

| Composition of Hardening Bath | |
|---|---|
| Sodium Hexametaphosphate | 1.0 g |
| Borax (hexahydrate) | 20.0 g |
| Formaldehyde (37% aq. soln.) | 10.0 ml |
| Water to make | 1 liter |

| Composition of Bleaching Solution | |
|---|---|
| Iron (III) Sodium Ethylenediaminetetraacetate (dihydrate) | 30.0 g |
| Potassium Bromide | 50.0 g |
| Disodium Ethylenediaminetetraacetate | 5.0 g |
| Boric Acid | 3.0 g |
| Borax | 1.5 g |
| Water to make | 1 liter |

| Composition of Fixing Solution | |
|---|---|
| Sodium Thiosulfate | 150 g |
| Sodium Sulfite | 15 g |
| Borax | 12 g |
| Glacial Acetic Acid | 15 ml |
| Potassium Alum | 20 g |
| Water to make | 1 liter |

The optical densities and the difference of green density $\Delta D^G$ of the samples thus-processed was determined as shown in FIG. 2. The results obtained are shown in Table 5 below. The value of $\Delta D^G$ is plus and a larger numerical value means larger interlayer effects.

Table 5

| Sample No. | Compound Layer Added | Compound | Amount (mol%) | Interlayer Effects $\Delta D^G$ |
|---|---|---|---|---|
| Control | | | | |
| 401 | GL | — | — | |
| | RL | — | — | −0.13 |
| Present Invention | | | | |
| 402 | GL | Compound (11) | 3 | |
| | RL | " | 6 | 0.21 |
| 403 | GL | Compound (1) | 3 | |
| | RL | " | 6 | 0.19 |
| Comparison | | | | |
| 404 | GL | DIR Coupler D-2 | 13 | |
| | RL | " | 25 | −0.06 |

As can be clearly understood from the results in Table 5, Samples 402 and 403 containing Compounds (11) and (1) of the present invention, respectively, show greater interlayer effects in comparison with Sample 404 containing Comparison Non-Color Forming DIR Coupler D-2.

EXAMPLE 5

Samples 401 to 404 prepared as described in Example 4 were exposed stepwise with white light (20 CMS) for 1/100 second and subjected to the color reversal processing as shown in the following.

| Processing Step | Temperature (°C.) | Time (min) |
|---|---|---|
| First Development (black-and-white) | 37° C. | 3 |
| Stopping Bath | " | 2 |
| Washing | " | 2 |
| Color Development (containing fogging agent) | " | 6 |
| Stopping Bath | " | 2 |
| Washing | " | 2 |
| Bleaching Bath | " | 6 |
| Washing | " | 2 |
| Fixing Bath | " | 2 |
| Washing | " | 2 |
| Stabilizing | " | 0.5 |
| Drying | " | |

| Composition of the First Developer Solution | |
|---|---|
| Sodium Sulfite | 60.0 g |
| 1-Phenyl-3-pyrazolidone | 0.3 g |
| Hydroquinone | 5.0 g |
| Sodium Carbonate (monohydrate) | 41.0 g |
| Potassium Bromide | 2.0 g |
| Potassium Iodide (1% aq. soln.) | 1.0 ml |
| Potassium Thiocyanate (1N aq. soln.) | 10.0 ml |
| Sodium Hydroxide (10% aq. soln.) | 2.0 ml |
| Water to make | 1 liter |
| Composition of Stopping Solution | |
| Sodium Acetate | 30 g |
| Glacial Acetic Acid | 8 ml |
| Water to make | 1 liter |
| Composition of Color Developer Solution | |
| Benzyl Alcohol | 5.0 ml |
| Sodium Hydroxide | 0.5 g |
| Diethylene Glycol | 3.0 ml |
| Sodium Hexametaphosphate | 2.0 g |
| Sodium Sulfite | 2.0 g |
| Potassium Bromide | 2.0 g |
| 4-Amino-3-methyl-N-ethyl-β-hydroxyethylaniline Sesquisulfate (monohydrate) | 10.0 g |
| Citrazinic Acid | 0.4 g |
| Metaboric Acid | 0.5 g |
| Sodium Metaborate (tetrahydrate) | 77.0 g |
| Sodium Borohydride | 0.1 g |
| Water to make | 1 liter |
| Composition of Bleaching Solution | |
| Iron (III) Sodium Ethylenediaminetetraacetate (dihydrate) | 100.0 g |
| Potassium Bromide | 150.0 g |
| Sodium Ethylenediaminetetraacetate | 5.0 g |
| Boric Acid | 3.1 g |
| Borax | 1.5 g |
| Water to make | 1 liter |
| Composition of Fixing Solution | |
| Sodium Thiosulfate | 150 g |
| Sodium Sulfite | 15 g |
| Borax | 12 g |
| Glacial Acetic Acid | 15 ml |
| Potassium Alum | 20 g |
| Water to make | 1 liter |
| Composition of Stabilizing Solution | |
| Formaldehyde (37% aq. soln.) | 10 ml |
| Water to make | 1 liter |

The graininess of the color image of each sample thus processed was measured using the conventional RMS (Root Mean Square) method using green light and red light. The results of RMS graininess at a density of 1.0 are shown in Table 6 below. The RMS graininess was measured with a measurement slit of $10\mu \times 10\mu$. The smaller is the numerical value the better is the graininess.

The measurement of the graininess of the RMS method is well known in the photographic art and is described in D Zeick & B. L. Brothers, Jr. "RMS Granularity; Determination of Just-noticeable Difference" *Photographic Science and Engineering*, vol. 19, No. 4 pp.235 to 238 (1975).

Table 6

| | RMS Graininess | |
|---|---|---|
| Sample No. | GL | RL |
| Control | | |
| 401 | 0.055 | 0.060 |
| Present Invention | | |
| 402 | 0.034 | 0.046 |
| 403 | 0.038 | 0.049 |
| Comparison | | |
| 404 | 0.052 | 0.058 |

From the results shown above it is apparent that Samples 402 and 403 which contain Compound (1) and (11) of the present invention, respectively, show a fine graininess as compared with Sample 401 which does not contain such compound or Sample 404 which contains Comparison DIR Coupler D-2.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive material comprising a support thereon having at least one silver halide emulsion layer containing a coupling compound represented by the following general formula (I):

wherein X represents

wherein $R_1$ represents a phenyl group which can be substituted with one or more substituents, which may be the same or different; R is an aromatic group represented by the general formula (II)

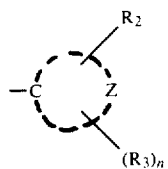

wherein Z represents an atomic group necessary to form, together with the carbon atom, an aryl group; $R_2$ represents a nitro group, a cyano group, an acyl group, an alkoxycarbonyl group, an aryloxycarbonyl group, a carbamoyl group, a sulfamoyl group, an alkylsulfonyl group, an arylsulfonyl group, an alkoxysulfonyl group, or an aryloxysulfonyl group; $R_3$ represents a hydrogen atom, a halogen atom, a nitro group, a cyano group, a thiocyano group, a hydroxy group, an alkoxy group, an aryloxy group, an alkyl group, an alkenyl group, an aryl group, an amino group, a carboxy group, an acyl group, an alkoxycarbonyl group, an aryloxycarbonyl group, a carbamoyl group, an acylamino group, a sulfo group, an alkylsulfonyl group, an arylsulfonyl group, an alkoxysulfonyl group, an aryloxysulfonyl group, a sulfamoyl group or a sulfonamido group and n represents an integer of 1 to 4; and wherein Y is a benzotriazole group which is bonded at the 1- or 2-position thereof and which is substituted by a group represented by the general formula (IIIA)

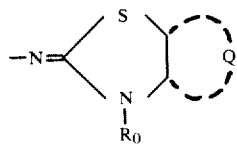

wherein $R_0$ represents an aliphatic group, an aralkyl group or an aryl group; and Q represents an atomic group necessary to form an aromatic ring, which can be substituted with one or more of an alkyl group, an alkoxy group and a halogen atom.

2. The photographic light-sensitive material as claimed in claim 1, wherein $R_1$, if substituted phenyl, is substituted with one or more substituents, which may be the same or different, selected from the group consisting of a halogen atom, a nitro group, a cyano group, a thiocyano group, a hydroxy group, a straight chain, branched chain or cyclic alkoxy group, a moncyclic or bicyclic aryloxy group having 6 to 20 carbon atoms, a straight chain, branched chain or cyclic alkyl group, a straight chain, branched chain or cyclic alkenyl group, a monocyclic or bicyclic aryl group, an amino group, a carboxy group, a straight chain, branched chain or cyclic acyl group, a straight chain, branched chain or cyclic alkoxycarbonyl group, a monocyclic or bicyclic aryloxycarbonyl group, a straight chain, branched chain or cyclic alkylcarbamoyl group, a monocyclic or bicyclic arylcarbamoyl group, a straight chain, branched chain or cyclic acylamino group, a sulfo group, a straight chain, branched chain or cyclic alkylsulfonyl group, a monocyclic or bicyclic arylsulfonyl group, a straight chain, branched chain or cyclic alkoxysulfonyl group, a monocyclic or bicyclic aryloxysulfonyl group, a sulfamoyl group, a sulfonamido group, or a divalent substituent which forms a condensed ring with the phenyl group.

3. The photographic light-sensitive material as claimed in claim 2, wherein the divalent substituent forms a condensed ring with the phenyl group forms a naphthalene ring.

4. The photographic light-sensitive material as claimed in claim 1, wherein Q forms an aromatic ring which is a phenyl group.

5. The photographic light-sensitive material as claimed in claim 4, wherein $R_0$ is said aliphatic group.

6. The photographic light-sensitive material as claimed in claim 1, wherein said silver halide emulsion layer further contains a color forming coupler.

7. The photographic light-sensitive material as claimed in claim 1, wherein said photographic light-sensitive material comprises a support having thereon a blue-sensitive silver halide emulsion layer containing a yellow color forming coupler, a green-sensitive silver halide emulsion layer containing a magenta color forming coupler and a red-sensitive silver halide emulsion layer containing a cyan color forming coupler, with at least one silver halide emulsion layer of the photographic light-sensitive material containing the coupling compound represented by the general formula (I).

* * * * *